US009616015B2

United States Patent
Charles

(10) Patent No.: US 9,616,015 B2
(45) Date of Patent: Apr. 11, 2017

(54) FORMULATIONS OF HUMAN TISSUE KALLIKREIN-1 FOR PARENTERAL DELIVERY AND RELATED METHODS

(71) Applicant: DiaMedica Inc., Winnipeg (CA)

(72) Inventor: Matthew Charles, St. Louis Park, MN (US)

(73) Assignee: DiaMedica Inc., Winnipeg (CA)

( * ) Notice: Subject to any disclaimer, the term of this patent is extended or adjusted under 35 U.S.C. 154(b) by 0 days.

(21) Appl. No.: 14/736,483

(22) Filed: Jun. 11, 2015

(65) Prior Publication Data

US 2016/0000704 A1 Jan. 7, 2016

Related U.S. Application Data

(63) Continuation of application No. 13/901,715, filed on May 24, 2013, now abandoned.

(60) Provisional application No. 61/652,069, filed on May 25, 2012, provisional application No. 61/791,762, filed on Mar. 15, 2013.

(51) Int. Cl.
*A61K 38/48* (2006.01)
*A61K 9/00* (2006.01)

(52) U.S. Cl.
CPC ........ *A61K 9/0019* (2013.01); *A61K 38/4853* (2013.01)

(58) Field of Classification Search
None
See application file for complete search history.

(56) References Cited

U.S. PATENT DOCUMENTS

| | | | |
|---|---|---|---|
| 3,472,931 A | 10/1969 | Stoughton | |
| 3,527,864 A | 9/1970 | MacMillan et al. | |
| 3,896,238 A | 7/1975 | Smith | |
| 3,903,256 A | 9/1975 | MacMillan et al. | |
| 3,952,099 A | 4/1976 | Smith | |

(Continued)

FOREIGN PATENT DOCUMENTS

| | | |
|---|---|---|
| CA | 2415392 A1 | 1/2002 |
| CA | 2465632 A1 | 5/2003 |

(Continued)

OTHER PUBLICATIONS

Lu et al., "Purification and characterization of human tissue prokallikrein and kallikrein isoforms expressed in Chinese hamster ovary cells", Protein Expression and Purification, vol. 8, pp. 227-237, 1996.*

(Continued)

*Primary Examiner* — Robert Mondesi
*Assistant Examiner* — Richard Ekstrom
(74) *Attorney, Agent, or Firm* — Cooley LLP

(57) ABSTRACT

Provided are high concentration compositions of tissue kallikrein-1 (KLK1) and methods of parenterally administering such compositions to a subject in need thereof, where absorption into the circulation via, for example, intravenous or subcutaneous administration improves systemic pharmacokinetics, bioavailability, safety, and/or convenience relative to intravenous or other forms of administration. Also provided are recombinant human KLK1 (rhKLK1) polypeptides that can be readily concentrated to high protein concentrations, and substantially pure compositions thereof.

10 Claims, 5 Drawing Sheets

(56) References Cited

U.S. PATENT DOCUMENTS

| | | |
|---|---|---|
| 4,046,886 A | 9/1977 | Smith |
| 4,130,643 A | 12/1978 | Smith |
| 4,130,667 A | 12/1978 | Smith |
| 4,146,613 A | 3/1979 | Dietze et al. |
| 4,150,121 A | 4/1979 | Dietze et al. |
| 4,299,826 A | 11/1981 | Luedders |
| 4,315,988 A | 2/1982 | Miwa et al. |
| 4,335,115 A | 6/1982 | Thompson et al. |
| 4,343,798 A | 8/1982 | Fawzi |
| 4,379,454 A | 4/1983 | Campbell et al. |
| 4,405,616 A | 9/1983 | Rajadhyaksha |
| 4,439,196 A | 3/1984 | Higuchi |
| 4,447,224 A | 5/1984 | DeCant, Jr. et al. |
| 4,447,233 A | 5/1984 | Mayfield |
| 4,474,893 A | 10/1984 | Reading |
| 4,475,196 A | 10/1984 | LaZor |
| 4,486,194 A | 12/1984 | Ferrara |
| 4,487,603 A | 12/1984 | Harris |
| 4,666,828 A | 5/1987 | Gusella |
| 4,676,980 A | 6/1987 | Segal et al. |
| 4,683,202 A | 7/1987 | Mullis |
| 4,689,042 A | 8/1987 | Sarnoff et al. |
| 4,746,515 A | 5/1988 | Cheng et al. |
| 4,788,062 A | 11/1988 | Gale et al. |
| 4,801,531 A | 1/1989 | Frossard |
| 4,816,567 A | 3/1989 | Cabilly et al. |
| 4,820,720 A | 4/1989 | Sanders et al. |
| 4,835,253 A | 5/1989 | Burton |
| 4,863,738 A | 9/1989 | Taskovich |
| 4,863,970 A | 9/1989 | Patel et al. |
| 4,925,678 A | 5/1990 | Ranney |
| 4,959,217 A | 9/1990 | Sanders et al. |
| 5,124,322 A | 6/1992 | Hughes |
| 5,167,616 A | 12/1992 | Haak et al. |
| 5,169,383 A | 12/1992 | Gyory et al. |
| 5,187,305 A | 2/1993 | Thompson et al. |
| 5,192,659 A | 3/1993 | Simons |
| 5,223,409 A | 6/1993 | Ladner et al. |
| 5,225,182 A | 7/1993 | Sharma |
| 5,234,956 A | 8/1993 | Lipton |
| 5,253,785 A | 10/1993 | Haber et al. |
| 5,262,430 A | 11/1993 | Borrevang et al. |
| 5,272,057 A | 12/1993 | Smulson et al. |
| 5,370,862 A | 12/1994 | Klokkers-Bethke et al. |
| 5,378,730 A | 1/1995 | Lee et al. |
| 5,403,484 A | 4/1995 | Ladner et al. |
| 5,403,486 A | 4/1995 | Leung |
| 5,462,739 A | 10/1995 | Dan et al. |
| 5,478,323 A | 12/1995 | Westwood et al. |
| 5,516,639 A | 5/1996 | Tindall et al. |
| 5,534,615 A | 7/1996 | Baker et al. |
| 5,561,165 A | 10/1996 | Lautt et al. |
| 5,571,698 A | 11/1996 | Ladner et al. |
| 5,580,576 A | 12/1996 | Veronesi et al. |
| 5,614,192 A | 3/1997 | Vandenbark |
| 5,648,095 A | 7/1997 | Illum et al. |
| 5,698,738 A | 12/1997 | Garfield et al. |
| 5,716,617 A | 2/1998 | Khandke et al. |
| 5,744,487 A | 4/1998 | Ohshima et al. |
| 5,762,922 A | 6/1998 | Noble et al. |
| 5,789,447 A | 8/1998 | Wink, Jr. et al. |
| 5,874,531 A | 2/1999 | Strominger et al. |
| 5,902,829 A | 5/1999 | Schneider et al. |
| 5,906,987 A | 5/1999 | Chwalisz et al. |
| 5,910,316 A | 6/1999 | Keefer et al. |
| 5,958,427 A | 9/1999 | Salzman et al. |
| 5,980,896 A | 11/1999 | Hellstrom et al. |
| 6,165,975 A | 12/2000 | Adams et al. |
| 6,171,232 B1 | 1/2001 | Papandreou et al. |
| 6,221,633 B1 | 4/2001 | Ertl et al. |
| 6,277,558 B1 | 8/2001 | Hudson |
| 6,288,040 B1 | 9/2001 | Muller et al. |
| 6,303,606 B1 | 10/2001 | Leonardi et al. |
| 6,307,027 B1 | 10/2001 | Linemeyer et al. |
| 6,358,536 B1 | 3/2002 | Thomas |
| 6,369,071 B1 | 4/2002 | Haj-Yehia |
| 6,436,996 B1 | 8/2002 | Vitek et al. |
| 6,492,405 B2 | 12/2002 | Haj-Yehia |
| 6,586,438 B2 | 7/2003 | Piper |
| 6,887,872 B2 | 5/2005 | Literati Nagy et al. |
| 6,962,793 B2 | 11/2005 | Diamandis |
| 7,087,247 B2 | 8/2006 | Li et al. |
| 7,195,759 B2 | 3/2007 | Sabbadini et al. |
| 7,622,447 B2 | 11/2009 | Lautt et al. |
| 7,723,326 B2 | 5/2010 | Lagu et al. |
| 8,058,019 B2 | 11/2011 | Roggenbuck |
| 9,364,521 B2 | 6/2016 | Charles et al. |
| 2001/0056068 A1 | 12/2001 | Chwalisz et al. |
| 2002/0106368 A1 | 8/2002 | Bot et al. |
| 2002/0192723 A1 | 12/2002 | Yoo |
| 2003/0045553 A1 | 3/2003 | Bussolari et al. |
| 2003/0114469 A1 | 6/2003 | Cohen |
| 2003/0158090 A1 | 8/2003 | Pedersen-Bjergaard et al. |
| 2003/0166662 A1 | 9/2003 | Fryburg et al. |
| 2003/0181461 A1 | 9/2003 | Lautt et al. |
| 2003/0216306 A1 | 11/2003 | Sabbadini et al. |
| 2003/0235609 A1 | 12/2003 | Lautt |
| 2004/0068005 A1 | 4/2004 | Szilvassy et al. |
| 2004/0151785 A1 | 8/2004 | Lautt |
| 2004/0209849 A1 | 10/2004 | Fischer |
| 2004/0253226 A1 | 12/2004 | Holaday et al. |
| 2005/0049293 A1 | 3/2005 | Lautt |
| 2007/0009438 A1 | 1/2007 | Lautt |
| 2007/0224209 A1 | 9/2007 | Berczi et al. |
| 2007/0238762 A1 | 10/2007 | Lautt |
| 2008/0004432 A1 | 1/2008 | Ruben et al. |
| 2009/0162342 A1 | 6/2009 | Berczi et al. |
| 2009/0233995 A1 | 9/2009 | Lautt |
| 2009/0324701 A1 | 12/2009 | Williams |
| 2010/0008899 A1 | 1/2010 | Williams |
| 2010/0226910 A1 | 9/2010 | Williams |
| 2011/0150781 A1 | 6/2011 | Charles et al. |
| 2012/0070425 A1 | 3/2012 | Williams et al. |
| 2012/0201804 A1 | 8/2012 | Williams et al. |
| 2012/0225051 A1 | 9/2012 | Williams |
| 2012/0276019 A1 | 11/2012 | Charles et al. |
| 2013/0089564 A1 | 4/2013 | Berczi et al. |
| 2013/0224230 A1 | 8/2013 | Berczi et al. |
| 2013/0280235 A1 | 10/2013 | Williams |
| 2013/0315891 A1 | 11/2013 | Charles et al. |
| 2013/0323222 A1 | 12/2013 | Charles et al. |
| 2014/0134152 A1 | 5/2014 | Willimas et al. |
| 2015/0196624 A1 | 7/2015 | Charles et al. |

FOREIGN PATENT DOCUMENTS

| | | |
|---|---|---|
| CA | 2659012 | 1/2008 |
| CN | 1384199 | 12/2002 |
| CN | 101255438 | 9/2008 |
| DE | 4420523 A1 | 12/1995 |
| DE | 102008003566 | 7/2009 |
| DE | 102008003568 | 7/2009 |
| EP | 0368187 | 9/1993 |
| EP | 0419504 | 1/1994 |
| EP | 0214826 | 10/1994 |
| EP | 0297913 | 2/1995 |
| EP | 0383472 | 2/1996 |
| EP | 0375437 | 9/1998 |
| EP | 0678522 | 1/2002 |
| EP | 0835139 | 9/2003 |
| EP | 0885961 | 12/2004 |
| GB | 1572146 | 7/1980 |
| JP | 56-115715 | 9/1981 |
| JP | 57-114512 | 7/1982 |
| WO | WO 89/00192 | 1/1989 |
| WO | WO 89/10937 | 11/1989 |
| WO | WO 91/17767 | 11/1991 |
| WO | WO 92/00321 | 1/1992 |
| WO | WO 00/07575 | 2/2000 |
| WO | WO 00/19992 | 4/2000 |
| WO | WO 00/53776 | 9/2000 |
| WO | WO 01/02039 | 1/2001 |
| WO | WO 01/36611 | 5/2001 |
| WO | WO 02/13798 | 2/2002 |

(56) References Cited

FOREIGN PATENT DOCUMENTS

| WO | WO 03/028730 | 4/2003 | | |
|---|---|---|---|---|
| WO | WO 2004/029238 | 4/2004 | | |
| WO | WO 2004/058258 | 7/2004 | | |
| WO | WO 2005/022146 | 3/2005 | | |
| WO | WO 2005/022164 | 3/2005 | | |
| WO | WO 2006/008002 | 1/2006 | | |
| WO | WO 2006/017538 | 2/2006 | | |
| WO | WO 2008/011713 | 1/2008 | | |
| WO | WO 2008/016883 | 2/2008 | | |
| WO | WO 2009/012571 | 1/2009 | | |
| WO | WO 2009039704 A1 * | 4/2009 | ........... | C12N 9/6445 |
| WO | WO 2010009557 A1 * | 1/2010 | ......... | A61K 38/4853 |
| WO | WO 2010080833 A1 * | 7/2010 | ............. | A61K 38/16 |
| WO | WO 2010/108262 | 9/2010 | | |
| WO | WO 2010/121358 | 10/2010 | | |
| WO | WO 2010/121361 | 10/2010 | | |
| WO | WO 2012/075342 | 6/2012 | | |
| WO | WO 2012/154574 | 11/2012 | | |
| WO | WO 2013/173923 | 11/2013 | | |
| WO | WO 2013/181755 | 12/2013 | | |
| WO | WO 2014/059536 | 4/2014 | | |

OTHER PUBLICATIONS

Yang et al., "Purification of human tissue prokallikrein excreted from insect cells by liquid chromatography", Journal of Pharmaceutical and Biomedical Analysis, vol. 39, pp. 848-852, 2005.*
Bodin et al., "Kallikrein protects against microalbuminuria in experimental type I diabetes", Kidney International, vol. 76, pp. 395-403, 2009.*
Pizard et al., "Genetic deficiency in tissue kallikrein activity in mouse and man: effect on arteries, heart and kidney", Biological Chemistry, vol. 389, pp. 701-706, 2008.*
Montanari et al., "Kallikrein gene delivery improves serum glucose and lipid profiles and cardiac function in streptozotocin-induced diabetic rats", Diabetes, vol. 54, pp. 1573-1580, 2005.*
Emanueli et al., "Prophylactic gene therapy with human tissue kallikrein ameliorates limb ischemia recovery in type 1 diabetic mice", Diabetes, vol. 53, pp. 1096-1103, 2004.*
Kolodka et al., "Preclinical characterization of recombinant human tissue kallikrein-1 as a novel treatment for type 2 diabetes mellitus", PLOS One, vol. 9, Issue 8: e103981, 2014.*
International Search Report and Written Opinion for International Application No. PCT/US2012/036556, mailed Aug. 30, 2012.
Supplementary European Search Report for European Application No. 13801165.5, mailed Feb. 8, 2016, 5 pages.
International Search Report and Written Opinion for International Application No. PCT/CA2013/050425, mailed Oct. 4, 2013.
Supplementary European Search Report for European Application No. 07784988.3, mailed Sep. 17, 2009.
International Search Report and Written Opinion for International Application No. PCT/CA2007/001321, mailed Nov. 30, 2007.
International Preliminary Report on Patentability for International Application No. PCT/CA2007/001321, dated Jan. 27, 2009.
Supplemental European Search Report for European Application No. 10755352.1, mailed Nov. 13, 2012.
International Search Report and Written Opinion for International Application No. PCT/CA2010/000413, mailed Jun. 7, 2010.
International Preliminary Report on Patentability for International Application No. PCT/CA2010/000413, dated Sep. 27, 2011.
International Search Report and Written Opinion for International Application No. PCT/CA2013/050395, mailed Sep. 19, 2013.
International Search Report and Written Opinion for International Application No. PCT/CA2013/050755, mailed Dec. 30, 2013.
Abdelaziz, A. et al., "Glucose homeostasis in the nonobese diabetic mouse at the prediabetic stage," Endocrinology, 139:1115-1124 (1998).
Abdelhaleem et al., "Identification of immunosuppressive fractions from the rat submandibular salivary gland," Immunology (1992) 76:331-337.

Adams, D. H. et al., "Transforming growth factor-β induces human T lymphocyte migration in vitro," The Journal of Immunology, Jul. 15, 1991;147(2):609-612.
Albertini, R. et al., "Kallikrein-kinin system in one- and two-kidney Goldblatt hypertensive rats," Clinical Science (Lond)., Mar. 1979;56(3):227-233.
Alhenc-Gelas et al., "Measurement of urinary kallikrein activity: Species differences in kinin production," Biochimica et Biophysica Acta (1981) 677:477-488.
Allen et al., "Rapid onset synovial inflammation and hyperplasia induced by transforming growth factor β," The Journal of Experimental Medicine, (1990) 171:231-247.
Angermann et al., "Purification and characterization of human salivary-gland prokallikrein from recombinant baculovirus-infected insect cells," Eur. J. Biochem. (1992) 206:225-233.
Assan et al., "Metabolic and Immunological Effects of Cyclosporin in Recently Diagnosed Type 1 Diabetes Mellitus," The Lancet, p. 67-71, Jan. 12, 1995.
Atkinson et al., "Islet Cell Autoantigens in Insulin-Dependent Diabetes," Adkinson and Maclaren, Islet Cell Autoangtigens in Diabetes, J Clin Invest 92, p. 1608-1616, 1993.
Atkinson, M. A. et al, "Type 1 diabetes: New perspectives on disease pathogenesis and treatment," Lancet 2001; 358:221-229.
Auger, I. et al., "New autoantigens in rheumatoid arthritis (RA): screening 8268 protein arrays with sera from patients with RA," Annals of the Rheumatic Diseases, 68:591-594 (2009).
Ausubel et al., "Current Protocols in Molecular Biology," 1989; cover page, title page and table of contents only, 22 pages.
Baggio, L. L. et al., "A recombinant human glucagon-like peptide (GLP)-1-albumin protein (albugon) mimics peptidergic activation of GLP-1 receptor-dependent pathways coupled with satiety, gastrointestinal motility, and glucose homeostasis," Diabetes, 53:2492-2500 (2004).
Barnett et al., "Treatment of rheumatoid arthritis with oral Type II Collagen," Arthritis & Rheumatism (1998) 41(2):290-297.
Baumgarten et al., "Concentrations of glandular kallikrein in human nasal secretions increase during experimentally induced allergic rhinitis," The Journal of Immunology (1986) 137(4):1323-1328.
Benson et al., "Oral administration of myelin basic protein is superior to myelin in suppressing established relapsing experimental autoimmune encephalomyelitis," The Journal of Immunology, 162:6247-6254 (1999).
Berczi et al., "The influence of pituitary hormones on adjuvant arthritis," Arthritis and Rheumatism (1984) 27(6):682-688.
Bhoola et al., "Bioregulation of kinins: Kallikreins, kininogens, and kininases," Pharmacological Reviews, 44(1):1-80 (1992).
Biosis Database [Online], Biosciences Information Service, Philadelphia, PA, Tschoepe Carsten et al., "Transgenic expression of human kallikrein prevents altered left ventricular function, the decline in sarcoplasmic reticulum calcium pump activity and the rise in cardiac collagen content in diabetic rats," Database accession No. PREV200100068837, Circulation, 102(18):II.267 (Oct. 31, 2000).
Bindseil et al., "Pure compound libraries; a new perspective for natural product based drug discovery," Drug Discovery Today, 6(16):840-847 (2001).
Blaukat, A. et al., "Regulation of Cardiovascular Signaling by Kinins and Products of Similar Converting Enzyme Systems—Downregulation of bradykinin B2 receptor in human fibroblasts during prolonged agonist exposure," American Journal of Physiology, Heart and Circulatory Physiology, 284(6):1909-1916 (2003).
Bork et al., "Increasing the sialylation of therapeutic glycoproteins: The potential of the sialic acid biosynthetic pathway," J Pharm Sci, Oct. 2009;98(10):3499-3508.
Bothwell, M. A. et al., "he relationship between glandular kallikrein and growth factor-processing proteases of mouse submaxillary gland," The Journal of Biological Chemistry, Aug. 10, 1979;254(15):7287-7294.
Brandes et al., "Type I transforming growth factor-β receptors on neutrophils mediate chemotaxis to transforming growth factor-β," The Journal of Immunology (1991) 147(5):1600-1606.
Caperuto et al., "Modulation of bone morphogenetic protein-9 expression and processing by insulin, glucose, and glucocorticoids:

(56) References Cited

OTHER PUBLICATIONS possible candidate for hepatic insulin-sensitizing substance," Endocrinology, 149(12):6326-6335 (2008).
Carlson, M. W. et al., "Chronic ulcerative stomatitis: evidence of autoimmune pathogenesis," Oral Surgery, Oral Medicine, Oral Pathology, Oral Radiology, and Endodontology, 111:742-748 (2011).
Swant, Inc., Catalog listing for Monoclonal anti-rat renin, [online], [Retrieved on Jan. 31, 2005], [Retrieved from the Internet: URL: http://www.swant.com/Antibodies_renin.htm, 1 page.
Chan, H. et al., "Expression and characterization of human tissue kallikrein variants," Protein Expr. and Purifi., Apr. 1998;12(3):361-370.
Chao, J. et al., "Experimental therapy with tissue kallikrein against cerebral ischemia," Frontiers in Bioscience, 11:1323-1327 (2006).
Chao, J. et al., "Functional analysis of human tissue kallikrein in transgenic mouse models," Hypertension, Mar. 1996;27(3 Pt 2):491-494.
Chatzigeorgiou et al., "The Use of Animal Models in the Study of Diabetes Mellitus," In Vivo, Mar.-Apr. 2009;23(2):245-258.
Chen et al., "Beneficial effects of kallikrein-binding protein in transgenic mice during endotoxic shock," Life Sciences (1997) 60(17):1431-1435.
Christensen, M. et al., "Lixisenatide, a novel GLP-1 receptor agonist for the treatment of type 2 diabetes mellitus," IDrugs, 12(8):503-513 (2009).
Christiansen et al., "Detection of tissue kallikrein in the bronchoalveolar lavage fluid of asthmatic subjects," J. Clin. Invest. (1987) 79:188-197.
Clements, J. et al., "The expanded human kallikrein (KLK) gene family: Genomic organization, tissue-specific expression and potential functions," Biological Chemistry, 382(1):5-14 (2001).
Clements, J. A., "The human kallikrein gene family: a diversity of expression and function," Molecular and Cellular Endocinology, 99:C1-C6 (1994).
Coker et al., " Role of hepatic α- and β-adrenergic receptor stimulation on hepatic glucose production during heavy exercise," American Journal of Physiology, Endocrinology and Metabolism, 273:E831-E838 (1997).
Croxatto, H. R. et al., "Inhibition of urinary kallikrein excretion by semi-purified renin in the rat," Clinical Science, 57:243s-245s (1979).
Cull et al., "Screening for receptor ligands using large libraries of peptides linked to C terminus of the lac repressor," PNAS, 89:1865-1869 (1992).
Cwirla et al., "Peptides on phage: A vast library ofpeptides for identifying ligands," Proc. Natl. Acad. Sci. USA, 87:6378-6382 (1990).
Damas, J. et al., "The kallikrein-kinin system, angiotensin converting enzyme inhibitors and insulin sensitivity," Diabetes/Metabolism Research and Reviews, 20(4):288-297 (2004).
Dertzbaugh et al., "Comparative effectiveness of cholera toxin B subunit and alkaline phosphatase as carriers for oral vaccines," Infection and Immunity (1993) 61(1):48-55.
Devasahayam, "Factors affecting the expression of recombinant glycoproteins," Indian J Med Research, Jul. 2007;126:22-27.
Devlin et al., "No excess of homozygosity at loci used for DNA fingerprinting," Science, 249 (4975):1416-1420 (1990).
DeWitt et al., "'Diversomers': An approach to nonpeptide, nonoligomeric chemical diversity," Proc. Natl. Acad. Sci. USA, 90:6909-6913 (1993).
Dodge, G. R. et al., "Immunohistochemical detection and immunochemical analysis of type II collagen degradation in human normal, rheumatoid, and osteoarthritic articular cartilages and in explants of bovine articular cartilage cultured with interleukin 1," J. Clin. Invest., 83:647-661 (1989).
Dong, Y. et al., "Tissue-specific promoter utilisation of the kallikrein-related peptidase genes, KLK5 and KLK7, and cellular localisation of the encoded proteins suggest roles in exocrine pancreatic function," Biological Chemistry, 389(2):1431-6730 (2008).
Doyle, B. L. et al., "Biophysical signatures of noncovalent aggregates formed by a glucagonlike peptide-1 analog: a prototypical example of biopharmaceutical aggregation," J. Pharm. Sci., 94(12):2749-2763 (2005).
Dunbar et al., "Central Adrenergic Suppression Augments the Insulin and Glucagon Secretory, and the Glycogenolytic Responses in Streptozotocin-Diabetic Rats," Hormone Research, 36:80-85 (1991).
Ebringer, A et al., "'B27 Disease' Is a New Autoimmune Disease That Affects Millions of People," Annals of the New York Academy of Sciences, 1110:112-120 (2007).
Edgerton et al., "Inhaled Insulin is Associated wth Prolonged Enhancement of Glucose Disposal in Muscle and Liver in the Canine," J Pharmacal Exp Ther., Mar. 2009; 328(3):970-975.
Eldefrawi et al., "Purification and molecular properties of the acetylcholine receptor from Torpedo Electroplax," Archives of Biochemistry and Biophysics, (1973) 159:362-373.
Ellingsgaard et al., "Interleukin-6 regulates pancreatic alpha-cell mass expansion," PNAS, 105(35):13162-13167 (2008).
Emami, N. et al., Utility of kallikrein-related peptidases (KLKs) as cancer biomarkers, Clinical Chemistry, 54(10):1600-1607 (2008).
Erb et al., "Recursive deconvolution of combinatorial chemical libraries," Proc. Natl. Acad. Sci. USA, 91:11422-11426 (1994).
Ericson et al., "Studies on the sicca syndrome in patients with rheumatoid arthritis," Acta. Rheum. Scand. (1970) 16: 60-80.
Weiner, H. L. et al.,"Oral tolerance," Immunol. Rev., 206:232-259 (Aug. 2005).
Fava et al., "Transforming growth factor β1 (TGF-β1) induced neutrophil recruitment to synovial tissues: Implications for TGF-β-driven synovial inflammation and hyperplasia," The Journal of Experimental Medicine (1991) 173:1121-1132.
FDA Guidance for Industry: Estimating the Maximum Safe Starting Dose in Initial Clinical Trial for Therapeutics in Adult Healthy Volunteers, Appendix D: Converting Animal doses to human equivalent doses, Jul. 2005; 30 pgs.
Felici, F., "Selection of antibody ligands from a large library of oligopeptides expressed on a multivalent exposition vector," J. Mol. Biol., 222:301-310 (1991).
Felson et al., "American College of Rheumatology preliminary definition of improvement in rheumatoid arthritis," Arthritis & Rheumatism (1995) 38(6): 727-735.
Ferreira et al., "Nitric oxide modulates eosinophil infiltration in antigen-induced airway inflammation in rats," European Journal of Pharmacology (1998) 358: 253-259.
Ferretti et al., "Intracolonic release of nitric oxide during trinitrobenzene sulfonic acid rat colitis," Digestive Dieseases and Sciences (1997) 42(12): 2606-2611.
Feutren et al., "Cyclosporin Increases the Rate and Length of Remission in Inuslin Dependent Diabetes of Recent Onset Results of a Multicentre Double-Blind Trial," The Lancet, p. 119-124 (1986).
Fiedler, F. et al., "Purification and properties of guinea-pig submandibular-gland kallikrein," Biochem. J., 209:125-134 (1983).
Figueroa, C. D. et al., "Cellular localization of human kininogens," Agents and Actions. Supplements 38(Pt. 1):617-626 (Jan. 1992).
Fodor et al., "Multiplexed biochemical assays with biological chips," Nature, 364:555-556 (1993).
Friberg et al., "Salivary kallikrein in Sjogren's syndrome," Clinical and Experimental Rheumatology (1988) 6:135-138.
Friedman, A. et al., "Induction of anergy or active suppression following oral tolerance is determined by antigen dosage," PNAS USA, 91:6688-6692 (Jul. 1994).
Fries et al., "The dimensions of health outcomes: The health assessment questionnaire, disability and pain scales," The Journal of Rheumatology (1982) 9(5):789-793.
Fuchtenbusch, M. et al., "Delay of Type 1 diabetes in high risk, first degree relatives by parenteral antigen administration: The Schwabing Insulin Prophylaxis Pilot Trial," Diabetologica, 41:536-541 (1998).

(56) References Cited

OTHER PUBLICATIONS

Fuller et al., "The cellular physiology of glandular kallikrein," Kidney International (1986) 29: 953-964.
Gallop et al., "Applications of combinatorial technologies to drug discovery. 1. Background and peptide combinatorial libraries," J. Med. Chem., 37(9):1233-1251 (1994).
Garrigue-Antar et al., "Optimisation of CCL64-based bioassay for TGF-β," Journal of Immunological Methods, (1995) 186:267-274.
Genbank Accession No. AAA39349 .1 National Center for Biotechnology Information, National Library of Medicine, National Institutes of Health, GenBank Locus AAA39349, Accession No. AAA39349, "Kallikrein 1 [Mus musculus domesticus]," [online]. Bethesda, MD [retrieved on Jun. 4, 2014]. Retrieved from the Internet:<URL:httn://www.ncbi.nlm.nih.gov/protein/AAA39349. 1>; 2 pages.
Genbank Accession No. AAI51559.1 National Center for Biotechnology Information, National Library ofMedicine, National Institutes of Health, GenBank Locus AAI51599, Accession No. AAI51559; Version No. AAI51559.1 GI:154426202, [online]. Bethesda, MD [retrieved on Aug. 11, 2014]. Retrieved from the Internet: <URL: http://www.ncbi.nlm.nih.gov/protein/154426202>; 2 pages.
Genbank Accession No. CAE51906.1National Center for Biotechnology Information, National Library ofMedicine, National Institutes ofHealth, GenBank Locus AE51906, Accession No. AE51906, "TPA: kallikrein 1 precursor [Rattus norvegicus]," [online]. Bethesda, MD [retrieved on Jun. 4, 2014]. Retrieved from the Internet:<URL: http://www /ncbi.nlm.nih. gov /protein/ CAE51906 .1 >; 2 pages.
Genbank Accession No. NP 002248.1 National Center for Biotechnology Information, National Library of Medicine, National Institutes of Health, GenBank Locus NP 002248, Accession No. NP 002248, "kallikrein-1 prepoprotein [*Homo sapiens*]," [online]. Bethesda, MD [retrieved on Jun. 4, 2014]. Retrieved from the Internet:<URL: http://wwww/ncbi.nlm.nih.gov/protein/NP 002248. 1>; 3 pages.
GenBank Accession No. AAH05313.1, Kallikrein 1 [*Homo sapiens*], Nov. 3, 2006.
GenBank Accession No. AAG11389.1, kallikrein [Mus musculus], Oct. 11, 2000.
GenBank Accession No. NP_113711.1, kallikrein-1 [Rattus norvegicus], Nov. 12, 2010.
Geterud et al., "Swallowing problems in rheumatoid arthritis," Acta Otolaryngol (Stockh) (1991) 111:1153-1161.
Giannoukakis, N., "Drug evaluation: BIM-51077, a dipeptidyl peptidase-IV-resistant glucagon-like peptide-1 analog," Curr. Opin. Investig. Drugs, 8(10):842-848 (2007).
Gimsa et al., "Type II collagen serology: A guide to clinical responsiveness to oral tolerance?" Rheumatol Int. (1997) 16:237-240.
Goodman, "Toward Evidence-Based Medical Statistics.2: The Bayes Factor," Ann Intern. Med, Jun. 15, 1999;130(12):1005-1013.
Gordon et al., "Applications of combinatorial technologies to drug discovery. 2. Combinatorial organic synthesis, library screening strategies, and future directions," J. Med. Chem., 37(10):1385-1401 (1994).
Grabley, S. et al., "8 tools for drug discovery: Natural product-based libraries," Ernst Schering Research Foundation Workshop, 32:217-252 (2000).
Graham et al., "Characteristics of a Human Cell Line Transformed by DNA from Human Adenovirus Type 5," J. Gen Viral., Jul. 1977;36:59-72.
Greaves et al., "Anionic salivary proteins associated with connective tissue disorders: sialated tissue kallikreins," Annals of the Rheumatic Diseases (1989) 48: 753-759.
Green, B. D. et al., "Novel glucagon-like peptide-1 (GLP-1) analog (Val$^8$)GLP-1 results in significant improvements of glucose tolerance and pancreatic β-Cell function after 3-week daily administration in obese diabetic (ob/ob) mice," The Journal of Pharmacology and Experimental Therapeutics, 318(2):914-921 (2006).

Griesbacher, T. et al., "Involvement of tissue kallikrein but not plasma kallikrein in the development of symptoms mediated by endogenous kinins in acute pancreatitis in rats," British J of Pharmacology, 137(5):692-700 (2002).
Griffiths et al., "Immunogenetic control of experimental Type II collagen-induced arthritis," Arthritis and Rheumatism (1981) 24(6): 781-789.
Hial, V. et al., "Purification and properties of a human urinary kallikrein (kininogenase)," Biochemistry, 13(21):4311-4318 (1974).
Harpel, P. C., "Studies on the interaction between collagen and a plasma kallikrein-like activity," J. Clin. Invest., 51:1813-1822 (1972).
Hernandez, C. C. et al., "Kininogen-kallikrein-kinin system in plasma and saliva of patients with Sjogren's syndrome," J. Rheumatol., 25:2381-2384 (1998).
Higashi et al., "Relationship Between Insulin Resistance and Endothelium-Dependent Vascular Relaxation in Patients with Essential Hypertension," Hypertension, 29:280-285 (1997).
Holz, "Giucagoi-Like Peptide-1 Synthetic Analogs: New Therapeutic Agents for Use in the Treatment of Diabetes Mellitus," Curr. Med Chem, 10(22):2471-2483 (2003).
Houghten et al., "Drug discovery and vaccine development using mixture-based synthetic combinatorial libraries," Drug Discovery Today, 5(7):276-285 (2000).
Houghten et al., "The use of synthetic peptide combinatorial libraries for the identification of bioactive peptides," Biotechniques, 13(3):412-421 (1992).
Hsu, C. C. et al., "Five cysteine-containing compounds delay diabetic deterioration in balb/cA mice," J. Nutr., 134(12):3245-3249 (2004).
Hu, Z. Q. al., "Enhancement of lymphocyte proliferation by mouse glandular kallikrein," Immunology Letters (1992) 32:85-90.
Ishizaka, K., "Twenty years with IgE: From the identification of IgE to regulatory factors for the IgE response," American Association of Immunologists Presidential Address, The Journal of Immunology (1985) 135(1): i-x.
Jaffa, A. A. et al., "Plasma Prekallikrein: A risk marker for hypertension and nephropathy in type 1 diabetes," Diabetes, 52(5):1215-1221 (2003).
Jaffa et al., "Induction of renal kallikrein and renin gene expression by insulin and IGF-1 in the diabetic rat," Diabetes, 1997;46:2049-2056.
James, M. N. et al., "Amino acid sequence alignment of bacterial and mammalian pancreatic serine proteases based on topological equivalences," Can. J. Biochem., 56(6):396-402 (1978).
Jensen et al., "Salivary acidic proline-rich proteins in rheumatoid arthritis," Ann NY Acad Sci. (1998) 842:209-211.
Jenzano et al., "The assay of glandular kallikrein and prekallikrein in human mixed saliva," Archs Oral Biol., (1988) 33(9):641-644.
Jong, Y.-J. et al., "Human bradykinin B2 receptors isolated by receptor-specific monoclonal antibodies are tyrosine phosphorylated," Proceedings of the National Academy of Sciences of the United States of America, 90(23):10994-10998 (1993).
Karaca et al., "Functional pancreatic beta-cell mass: involvement in type 2 diabetes and therapeutic intervention," Diabetes Metab., 65:77-84 (2009).
Kehrl et al., "Further studies of the role of transforming growth factor-β in human B cell function," The Journal of Immunology, (1989) 6:1868-1874.
Kehrl et al., "Transforming growth factor-β suppresses human B lymphocyte Ig production by inhibiting synthesis and the switch from the membrane form to the secreted form of Ig mRNA," The Journal of Immunology (1991) 146:4016-4023.
Kelly et al., "Decreased salivary epidermal growth factor in rheumatoid disease: a possible mechanism for increased susceptibility to gastric ulceration," Brit. Med. J., (1990) 301:422-423.
Kellermann, Jr. et al., "Human urinary kallikrein-amino acid sequence and carbohydrate attachment sites," Protein Seq Data Anal., Feb. 1988; 1(3):177-182.
Kemp et al., "Suppression and enhancement of in vitro lymphocyte reactivity by factors in rat submandublar gland extracts," Immunology (1985) 56:261-267.

(56) References Cited

OTHER PUBLICATIONS

Kemp et al., "Inhibition of interleukin I activity by a factor in submandibular glands of rats," The Journal of Immunology (1986) 137(7):2245-2251.
Kerby et al., "Salivary kallikrein levels in normal and in rheumatoid individuals," J Lab Clin Med. (1968) 71(4):704-708.
Kim, J. K. et al., "Multiple sclerosis: An Important Role for Post-Translational Modifications of Myelin Basic Protein in Pathogenesis," Molecular and Cellular Proteomics, 2:453-462 (2003).
Kim, Y. et al., "Identification of Hnrph3 as an autoantigen for acute anterior uveitis," Clinical Immunology, 138:60-66 (2011).
Knoerzer et al., "Collagen-induced arthritis in the BB rat," J. Clin. Invest. (1995) 96:987-993.
Kremer, J. M., "Methotrexate and emerging therapies," Rheumatic Diseases Clinics of North America (1998) 24(3):651-658.
Kroon et al., "The transcriptional regulatory strategy of the rat tissue kallikrein gene family," Genes Funct., Dec. 1997;1(5):309-319.
Lam et al., "A new type of synthetic peptide library for identifying ligand-binding activity," Nature, 354:82-84 (1991).
Lampeter, E. F. et al., "The Deutsche Nicotinamide Intervention Study: An Attempt to Prevent Type 1 Diabetes," Diabetes, 47:980-984 (1998).
Larsen et al., "Individual variations of pH, buffer capacity, and concentrations of calcium and phosphate in unstimulated whole saliva," Archives of Oral Biology (1999) 44:111-117.
Lautt, W. W. et al., "Rapid insulin sensitivity test (RIST)," Can. J. Physiol. Pharmacol., 76:1080-1086 (1998).
Lautt, W. W., "The HISS story overview: a novel hepatic neurohumoral regulation of peripheral insulin sensitivity in health and diabetes," Canadian Journal of Physiology Pharmacology, 77:553-562 (1999).
Lautt, W. W. et al., "Hepatic parasympathetic (HISS) nerve-dependent control of peripheral insulin sensitivity is determined by feeding and fasting: dynamic control of HISS-dependent insulin action," American Journal of Physiology—Gastrointestinal and Liver Physiology, 281:G29-G36 (2001).
Lautt, W., "A new paradigm for diabetes and obesity: the hepatic insulin sensitizing substance (HISS) hypothsis," J. Pharmacol. Sci., 95(1):9-17 (2004).
LaxmiKanthan et al., "1.70 A X-Ray Structure of Human apo Kallikrein 1: Structural Changes Upon Peptide Inhibitor/Substrate Binding," Proteins: Structure, Function, and Bioinformatics, 58:802-814 (2005).
Leger, R. et al., "Identification of CJC-1131-albumin bioconjugate as a stable and bioactive GLP-1(7-36) analog.," Bioorg. Med. Chem. Lett., 14(17):4395-4398 (2004).
Lee et al., "Co-stimulation of T cell proliferation by transforming growth factor-β1," The Journal of Immunology (1991) 147(4):1127-1133.
Lenander-Lumikari et al., "Stimulated salivary flow rate and composition in asthmatic and non-asthmatic adults," Archives of Oral Biology, 43:151-156 (1998).
Li, H. et al., "Substrate specificity of human kallikreins 1 and 6 determined by phage display," Protein Science, 17:664-672 (2008).
Li, H. et al., "Tissue kallikrein protects against pressure overload-induced cardiac hypertrophy through kinin B2 receptor and glycogen synthase kinase-3β activation," Cardiovascular Research, 73(1):130-142 (2007).
Lin, F-K. et al., "Molecular cloning and sequence analysis of the monkey and human tissue kallikrein genes," Biophys. Biochem. Acta, 1173:325-328 (1993).
Lindsay et al., "Inhibition of dipeptidyl peptidase IV activity by oral metformin in Type 2 diabetes," Diabetic Medicine, 22:654-657 (2005).
Logan, J. et al., "Adenovirus tripartite leader sequence enhances translation of mRNAs later after infection," PNAS USA, Jun. 1984;81(12):3655-3659.
Lu, H. S. et al., "Human urinary kallikrein: complete amino acid sequence and sites of glycosylation," Int. J Peptide Protein Res., 1989;33:237-249.

Majewska et al., "Epicutaneous immunization with myelin basic protein protects from the experimental autoimmune encephalomyelitis," Pharmalogical Reports, (2007) 59 74-79.
Montanari, D. et al., "Kallikrein gene delivery improves serum glucose and lipid profiles and cardiac function in streptozotocin-induced diabetic rats," Diabetes, 54:1573-1580 (2005).
Manto, A. et al., "Urinary kallikrein excretion in Type 1 (insulin-dependent) diabetes mellitus," Diabetologia, 36(5):423-427 (1993).
Material Safety Data Sheet, Azo dye-impregnated collagen, Sigma-Aldrich (version 4.0), Feb. 27, 2010.
Mather, "Establishment and Characterization of Two Distinct Mouse Testicular Epithelial Cell Lines," Biol Reprod., Aug. 1, 1980;23 :243-251.
Mather et al., "Culture of Testicular Cells in Hormone-Supplemented Serum-Free Medium," Annals NY Acad Sci, Jun. 1982:383:44-68.
Matsushita, S. et al., "Biphasic effect of kallikrein on IgE and IgGI syntheses by LPS/IL4-stimulated B-cells," Cellular Immunology, 146:210-214 (1993).
Matthews et al., "Salivary secretion and connective tissue disease in man," Annals of the Rheumatic Diseases, (1985) 44: 20-26.
Mayfield, R. K. et al., "Skeletal muscle kallikrein. Potential role in metabolic regulation," Diabetes, Jan. 1996;45 Suppl 1:S20-S23.
Mazzone, P et al., "Our new understanding of pulmonary alveolar proteinosis: What an internist needs to know," Cleveland Clinic Journal of Medicine, 68: 977-978 (2001).
McCartney-Francis et al., "Transforming growth factor β: a matter of life and death," Journal of Leukocyte Biology (1994) 55:401-409.
McCormack et al., "Molecular forms of prostate-specific antigen and the human kallikrein gene family: A new era," Urology (1995) 45(5):729-744.
McIntosh et al., "Antigen-specific suppressor macrophages induced by culture with cyclosporine A plus acetoylcholine receptor," Journal of Neuroimmunology (1989) 25:75-89.
McIntosh et al., "Tolerance to acetylcholine receptor induced by AChR-coupled syngeneic cells," Journal of Neuroimmunology (1992) 38:75-84.
Medline Plus, Type 1 Diabetes, U.S. National Library of Medicine, NIH, [online], [Retrieved on Aug. 28, 2013], [Retrieved from the Internet: URL: <http://www.nlm.nih.gov/medlineplus/ency/article/000305.htm>], 7 pages.
Meier, J. J., "Beta cell mass in diabetes: a realistic therapeutic target?," Diabetologia, 51(5):703-713 (2008).
Merrifield, "Solid Phase Peptide Synthesis. I. The Synthesis of a Tetrapeptide," J Am Chem Soc., 1963;85(14):2149-2154.
Miranda et al., "The amidase activity of human tissue kallikrein is significantly higher in the urine of patients with either type 1 or gestational diabetes mellitus," Int. J. Diabetes & Metab., 18:124-131 (2010).
Moore, M. C. et al., "Effect of hepatic denervation on peripheral insulin sensitivity in concious dogs," American Journal of Physiology—Endocrinology and Metabolism, 282:E286-296 (2002).
Moreau, M. E. et al., "The kallikrein-kinin system: current and future pharmacological targets," Journal of Pharmacological Sciences, Sep. 2005;99(1):6-38.
Morris et al., "Hapten-induced model of chronic inflammation and ulceration in the rat colon," Gastroenterology (1989) 96:795-803.
Moser, A. et al, "Beta cell antigens in type 1 diabetes: triggers in pathogenesis and therapeutic targets," F1000 Biology Reports 2010, 2:75 (doi:10.3410/B2-75), 4 pages.
Nagy, E. et al., "Immunoregulatory effects of glandular kallikrein from the salivary submandibular gland of rats," Neuroimmunomodulation (1997) 4:107-112.
Naslund, E. et al., "Glucagon-like peptide-1 analogue LY315902: effect on intestinal motility and release of insulin and somatostatin," Regul. Pept., 106(1-3):89-95 (2002).
Nathan, D. M. et al., "Medical Management of Hyperglycemia in Type 2 Diabetes: A Consensus Algorithm for the Initiation and Adjustment of Therapy," Diabetes Care, 32(1):193-203 (2009).
Naughton, M. A. et al., "Esteropeptidase and thymotropic activity of a protein isolated from the mouse submaxillary gland," Biochimica et Biophysica Acta (1972) 263:106-114.

(56) References Cited

OTHER PUBLICATIONS

Norris, S. L. et al., "Drug class review: Newer drugs for the treatment of diabetes mellitus," Final Report, Aug. 2008, Oregon Health & Science University, Portland, Oregon (2008).
Ole-Moi et al., "Structural studies of a human urinary kallikrein (urokallikrein)," PNAS, Jul. 1979;76(7):3121-3125.
OriGene, "KLK1 (NM_002257) Human cDNA Clone," [online], [Retrieved on Feb. 18, 2012], [Retrieved from the Internet: <URL: http://www.origene.com/human_cdna/NM_002257/SC122623/KLK1.aspx>], 1 page.
Oza et al., "A Simple High-Yield Procedure for Isolation of Human Urinary Kallikreins," Biochem J, Apr. 1, 1978;171(1): 285-288.
Ottlecz, A. et al., "Plasmakinin system in alloxan diabetic rats," Adv. Biosci., 17:57-63 (1978).
Perris, A. D., et al., "The mitogenic action of bradykinin on thymic lymphocytes and its dependence on calcium," Proc. Soc. Exp. Biol. Med., 130:1198-1201 (1969).
Predki, P. et al., "Protein microarrays: A new tool for profiling antibody cross-reactivity," Human Antibodies, 14:7-15 (2005).
Proud et al., "Kinins are generated in vivo following nasal airway challenge of allergic individuals with allergen," J. Clin. Invest. (1983) 72:1678-1685.
Rader, C., "Antibody libraries in drug and target discovery," Drug Discovery Today, 6(1):36-43 (2001).
Rajapakse et al., "Estrogen-dependent expression of the tissue kallikrein gene (Klk1) in the mouse uterus and its implications for endometrial tissue growth," Mol Reprod Dev, Aug. 2007;74(8):1053-1063.
Recombinant Human Kallikrein-1/ KLK1. Datasheet [online] SinoBiological Inc., 2011 [retrieved on Aug. 14, 2013]. [Retrieved from the Internet: <URL:http://web.archive.org/web/20110911225357/http://www.sinobiological.com/KLK1-Protein-g-284.html>]; 4 pages.
Reibman et al., "Transforming growth factor β1, a potent chemoattractant for human neutrophils, bypasses classic signal-transduction pathways," Proc. Natl. Acad. Sci. (1991) 88:6805-6809.
Remington: The Science and practice of Pharmacy, Mack Publishing Company, Easton, PA, Edition 21; 2005; cover page, title page and table of contents only.
Richards, R. I. et al., Mouse glandular kallikrien genes, The Journal of Biological Chemistry, 257(6):2758-2761 (1982).
Roberts et al., "New class of transforming growth factors potentiated by epidermal growth factor: Isolation from non-neoplastic tissues," Proc. Natl. Acad. Sci. (1981) 78(9):5339-5343.
Roberts et al., "The transforming growth-factor-βs," Handbook of Pharmacology 95(1990):Chapter 8:419-472.
Robinson et al., "Transfer of human serum IgG to nonobese diabetic Igμnull mice reveals a role for autoantibodies in the loss of secretory function of exocrine tissues in Sjogren's syndrome," Proc. Natl. Acad. Sci. (1998) 95: 7538-7543.
Rothschild, A. M. et al., "Increased kininogen levels observed in plasma of diabetic patients are corrected by the administration of insulin," Hormone and Metabolic Research, 31(5):326-328 (1999).
Russell et al., "Investigation of xerostomia in patients with rheumatoid arthritis," JADA (1998) 129: 733-739.
Sabbadini et al., "The submandibular gland: A key organ in the neuro-immuno-regulatory network?" Neuroimmunomodulation, 2:184-202 (1995).
Sagara, T. et al., "Reduction of collagen type 1 in the ciliary muscle of inflamed monkey eyes," Investigative Ophthalmology & Visual Science, 40:2568-2576 (1999).
Salgame et al., "Differing lymphokine profiles of functional subsets of human CD4 and CD8 cell clones," Science (1991) 254 (5029): 279-282.
Sambrook et al., "Molecular Cloning, A Laboratory Manual," 2nd Edition. 1989; Cold Spring Harbor Laboratory Press, Nina Irwin; Table of Contents Only; 31 pages.
Sambrook et al., "Molecular Cloning, A Laboratory Manual," 3rd Edition. 2001; Table of Contents Only 22 pages.
Sartor et al., "Selective kallikrein-kinin system activation in inbred rats differentially susceptible to granulomatous enterocolitis," Gastroenteroloy (1996) 110:1467-1481.
Schubert-Zsilavecz, M. et al., Insulin glargin—ein langwirksames Insulinanalogon: Bessere Blutzuckerwerte beim Diabetiker, Pharmazie in unserer Zeit, Mar. 2001;30(2):125-130.
Scott et al., "Searching for peptide ligands with an epitope library," Science, 249 (4967):386-390 (1990).
Shaw, J. et al., "Regulation of human tissue kallikrein-related peptidase expression by steroid hormones in 32 cell lines," Biological Chemistry, 389(11):1409-1419 (2008).
Simson, J. A. V. et al., "Histopathology of lymphatic tissue in transgenic mice expressing human tissue kallikrein gene," Lab. Invest., 71:680-687 (1994).
Simson, J. A. V., "Localization of kallikrein gene family proteases in rat tissues," Agents and Actions-Suppl., 38(1):595 (1992).
Slim, R. et al., "Loss-of-function polymorphorphism of the human kallikrein gene with reduced urinary kallikrein activity," J. Am. Soc. Nephrol., 2002; 13:968-976.
Song et al., "The thymus plays a role in oral tolerance in experimental autoimmune encephalomyelitis," The Journal of Immunology (2006) 177:1500-1509.
Song, G. et al., "New Centromere Autoantigens Identified in Systemic Sclerosis Using Centromere Protein Microarrays," Journal of Rheumatology, 40:461-468 (2013).
Spinetti, G. et al., "Tissue kallikrein is essential for invasive capacity of circulating proangiogenic cells," Circulation Research, 108(3):284-293 (Feb. 2011), doi: 10.1161/CIRCRESAHA.110.236786. Epub Dec. 16, 2010.
Steinbrocker et al., "Therapeutic criteria in rheumatoid arthritis," The Journal of the American Medical Association (1949) 140(8):659-662.
Sun, H. et al., "Prolonged hypotensive effect of human tissue kallikrein gene delivery and recombinant enzyme administration in spontaneous hypertension rats," Experimental and Molecular Medicine, 36(1):23-27 (2004).
Swift, G. H. et al., "Rat pancreatic kallikrein mRNA: Nucleotide sequence and amino acid sequence of th encoded preproenzyme," Proc. Nat. Acad. Sci. U.S.A., 79:7263-7267 (1982).
Synopsis "Type 2 Diabetes: Insulin Resistance May Be the Result of Mitochondrial Dysfunction.," PLOS Med 2(9): e292, 2 pages (2005).
Szodoray, P. et al., "Anti-citrullinated protein/peptide autoantibodies in association with genetic and environmental factors as indicators of disease outcome in rheumatoid arthritis," Autoimmunity Reviews, 9:140-143 (2010).
Takada, K. et al., "Autoimmunity against a tissue kallikrein in IQI/Jic mice: a model for Sjogren's syndrome," J. Biol. Chem., 280:3982-3988 (2005).
Takayama et al., "Characterization of the precursor of prostate-specific antigen," The Journal of Biological Chemistry (1997) 272(34):21582-21588.
Teitelbaum et al., "Immunomodulation of experimental autoimmune encephalomyelitis by oral administration of copolymer I," Proc. Natl. Acad. Sci. USA (1999) 96: 3842-3847.
Teva Marion, "Copaxone (glatiramer acetate injection)," [online], [Retrieved on the internet: URL:<http://www.msakc.org/Articles/Copaxone.htm>, [Retrieved on Jul. 31, 2008], 4 pages.
Teva Pharmaceutical Industries Ltd., "Copaxone (glatiramer acetate injection)," Package Insert (May 2007), 4 pages.
[No author listed], "The effect of intensive treatment of diabetes on the development and progression of long-term complications in insulin-dependent diabetes mellitus. The Diabetes Control and Complications Trial Research Group," N. Engl. J. Med., Sep. 30, 1993;329(14):977-986.
Thorkildsen, C. et al., "Glucagon-like peptide 1 receptor agonist ZP10A increases insulin mRNA expression and prevents diabetic progression in db/db mice," The Journal of Pharmacology and Experimental Therapeutics, 307(2):490-496 (2003).
Tian, L. et al., "Reversal of New-Onset Diabetes through Modulating Inflammation and Stimulating β-Cell Replication in Non-obese Diabetic Mice by a Dipeptidyl Peptidase IV Inhibitor," Endocrinology, Jul. 2010, 151(7):3049-3060.

(56) References Cited

OTHER PUBLICATIONS

Trautschold, I., "Assay methods in the kinin system," Handbook of Experimental Pharmacoloy (1970) 25: 52-81.

Trentham, D. E., "Oral tolerization as a treatment of rheumatoid arthritis," Rheumatic Diseases Clinics of North America (1998) 24(3): 525-536.

Tschetsche, H. et al., "The primary structure of porcine gladular kallikreins," Adv. Exp. Med. Biol., 120A:245-260 (1979).

Tschope et al., "Functional, biochemical, and molecular investigations of renal kallikrein-kinin system in diabetic rats," Am. J. Physiol. Heart Circ. Physiol., 277:H2333-H2340 (1999).

Uehara, S. et al., "Kallikrein-kinin system in diabetic patients," Drug. Res., 38(5):721-723 (1988).

UniProtKB/Swiss-Prot Accession No. P06870; May 14, 2014, [Retrieved from the internet: URL:<www.uniprot.org/uniprot/P06870>], [Retrieved on May 3, 2014].

Urlaub, G. et al., "Isolation of Chinese hamster cells mutants deficient in dihydrofolate Reductase activity," Proc Natl Acad Sci U S A. Jul. 1980; 77(7): 4216-4220.

Verwaerde, C. et al., "Properties of serine proteases of Schistosoma mansoni Schistosomula involved in the regulation of IgE synthesis," Scand. J. Immunol. (1988) 27:17-24.

Vojdani et al., "Methyl tertiary-butyl ether antibodies among gasoline service station attendants," Ann. NY Acad. Sci., 837:96-104 (1997) (Abstract).

Wahl et al., "Transforming growth factor type β induces monocyte chemotaxis and growth factor production," Proc. Natl. Acad. Sci. (1987) 84: 5788-5792.

Wahl, S. M., "Transforming growth factor beta (TGF-β) in inflammation: A cause and a cure," Journal of Clinical Immunology (1992) 12(2):61-74.

Wahren, J. et al., "Role of C-peptide in human physiology," Am. J. Physiol. Endocrinol. Metab., 278(5):E759-E768 (2000).

Walker et al., "Interaction of human IgG chimeric antibodies with the human FcRI and FcRII receptors: Requirements for antibody-mediated host cell-target cell interaction," Molecular Immunology, 26(4):403-411 (1989).

Wang et al., "Investigation of the clinical value of total saliva flow rates," Archives of Oral Biology (1998) 43:39-43.

Watson, E. et al., "Comparison of N-linked oligosaccharides of recombinant human tissue kallikrein produced by Chinese hamster ovary cells on microcarrier beads and in serum-free suspension culture," Biotechnol. Prog., Jan.-Feb. 1994;10(1):39-44.

Weinblatt et al., "Efficacy of low-dose methotrexate in rheumatoid arthritis," The New England Journal of Medicine (1985) 312(13):818-822.

Weiner, H. L., "Oral tolerance for the treatment of autoimmune diseases," Annu. Rev. Med., 48:341-351 (1997).

Weiner, H. L. et al., "Oral tolerance: immunologic mechanisms and treatment of animal and human organ-specific autoimmune diseases by oral administration of autoantigens," Annu. Rev. Immunol., 12:809-837 (1994).

Weiner, H.L., "Oral tolerance with Copolymer 1 for the treatment of multiple sclerosis," Proc. Natl. Acad. Sci. USA (1999) 96: 3333-3335.

Weiner, H. L., "Oral tolerance: immune mechanisms and treatment of autoimmune diseases," Immunol. Today, 18(7):335-343 (1997).

Weir et al., "Five Stages of Evolving β-Cell Dysfunction During Progression to Diabetes," Diabetes, 53(3):S16-S21 (2004).

Wikipedia, "Kidney" [online], [Retrieved on Jan. 31, 2005], [Retrieved from the Internet: URL:<http://www.wikipedia.org/wiki/Kidney>], 5 pages.

Wilson, R. D. et al., "Fructose-fed streptozotocin-injected rat: an alternative model for type 2 diabetes," Pharmacological Reports, v.64, pp. 129-139 (2012).

Wines, D. R. et al., "Organization and expression of the rat kallikrein gene family," J. Biol. Chem., 264(13):7653-7662 (1989).

Wolinsky, J. S., "The use of glatiramer acetate in the treatment of multiple sclerosis," Adv. Neural. (2006) 98:273-92 (Abstract).

Yamamura et al., "Defining protective responses to pathogens: Cytokine profiles in leprosy lesions," Science (1991) 254(5029):277-279.

Yao et al., "Tissue kallikrein infusion prevents cardiomyocyte apoptosis, inflammation and ventricular remodeling after myocardial infarction," Regulatory Peptides, 140(1-2):12-20 (2007).

Yao, Y. et al., "Tissue kallikrein promotes neovascularization and improves cardic function by the Akt-glycogen synthase kinase-3β pathway," Cardiovascular Research, 80(3):354-364 (2008).

Yin et al., "Kallikrein/kinin protects against myocardial apoptosis after ischemia/reperfusion via akt-glycogen synthase kinase-3 and Akt-Bad-14-3-3 signaling pathways," The Journal of Biological Chemistry, 280(9):8022-8030 (2005).

Yki-Jarvinen, "Combination Therapies with Insulin in Type 2 Diabetes," Deabetes Care, 24(4):758-767 (2001).

Yost et al., "Tandem quadrupole mass spectrometry," In: Tandem Mass Spectrometry, McLafferty (Ed.), Wiley & Sons, New York, pp. 175-195 (1983).

Yousef, G. M. et al., "The new human tissue kallikrein gene family: structure, function, and association to disease," Endocrine Reviews, Apr. 2001;22(2):184-204.

Yousef, G. M. et al., "Molecular cloning of the human kallikrein 15 gene (KLK15)," J. Biol. Chem., 276(1):53-61 (2001).

Yousef, G. et al., "Genomic organization of the human kallikrein gene family on chromosome 19q13.3-q13.4," Biochemical and Biophysical Research Communications, 276(1):125-133 (2000).

Yousef, G. et al., "In-silico analysis of kallikrein gene expression in pancreatic and colon cancers," Anticancer Research, 24(1):43-51 (2004).

Yuan, G. et al., "Tissue Kallikrein Reverses Insulin Resistance and Attenuates Nephropathy in Diabetic Rats by Activation of Phosphatidylino sitol 3-Kinase/Protein Kinase B and Adenosine 5-Monophosphate-Activated Protein Kinase SiQnalinQ Pathways," Endocrinology, 148(5):2016-2026 (2007).

Zhao et al., "A coding polymorphism of the kallikrein 1 gene is associated with essential hypertension: a tagging SNP-based association study in a chinese Han population," J. Hypertens., 25:11821-1827 (2007).

Zhao et al., "Gene therapy with human tissue kallikrein reduces hypertension and hyperinsulinemia in fructose-induced hypertensive rats," Hypertension, 42:1026-1033 (2003).

\* cited by examiner

FORMULATIONS OF HUMAN TISSUE KALLIKREIN-1 FOR PARENTERAL DELIVERY AND RELATED METHODS

CONTINUING APPLICATION DATA

This application is a continuation application of U.S. patent application Ser. No. 13/901,715, filed on May 24, 2013, which claims the benefit of U.S. Provisional Application Ser. No. 61/652,069, filed May 25, 2012, and U.S. Provisional Application Ser. No. 61/791,762, filed Mar. 15, 2013, each of which is incorporated by reference herein.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DIAM_030_03US_SeqList_ST25. The text file is about 6 KB, was created on Sep. 22, 2015, and is being submitted electronically via EFS-Web.

BACKGROUND

In healthy individuals, insulin release by the pancreas is strictly coupled to the blood glucose concentration. Elevated blood glucose levels like those occurring after meals are rapidly compensated by a corresponding rise in insulin secretion. Diabetes mellitus, or simply diabetes, is a group of metabolic diseases in which a person has high blood sugar, either because the pancreas does not produce enough insulin, or because cells do not respond to the insulin that is produced. Around 366 million people worldwide suffer from diabetes mellitus. Untreated, diabetes can cause many complications. Acute complications include diabetic ketoacidosis and nonketotic hyperosmolar coma. Serious long-term complications include cardiovascular disease, chronic renal failure, diabetic retinopathy, and diabetic neuropathy. The adequate treatment of diabetes is thus important and there is a need for improved therapies for the treatment of diabetes. Furthermore, there is an ongoing need for efficient and safe formulations for the administration of therapies for the treatment of diabetes.

SUMMARY OF THE INVENTION

The present invention includes a composition formulated for parenteral administration, the composition having a human tissue kallikrein-1 (hKLK1) polypeptide and a pharmaceutically acceptable carrier, wherein the concentration of the hKLK1 polypeptide in the composition is greater than about 5 mg/mL. In some embodiments, the hKLK1 polypeptide has a pI of less than about 5 and a sialic acid content of at least about 4 moles per mole protein. In some embodiments, the hKLK1 concentration is greater than about 10 mg/mL. In some embodiments, the hKLK1 concentration is greater than about 25 mg/mL. In some embodiments, the composition is substantially free of aggregates (greater than about 95% appearing as a single peak by SEC HPLC). In some embodiments, the composition has endotoxin levels of less than about 1 EU/mg protein, host cell protein of less than about 100 ng/mg protein, host cell DNA of less than about 10 pg/mg protein. In some embodiments, the hKLK1 has an amino acid sequence with at least about 95% sequence identity to residues 25-262 of SEQ ID NO:1 or SEQ ID NO:2 and has serine protease activity. In some embodiments, the serine protease activity is characterized by the ability to release kallidin from a higher molecular weight precursor. In some embodiments, the hKLK1 polypeptide includes E145 and/or A188, relative to SEQ ID NO:1. In some embodiments, the hKLK1 polypeptide includes Q145 and/or V188, relative to SEQ ID NO:1. In some embodiments, the hKLK1 polypeptide includes residues 25-262 of SEQ ID NO:2.

The present invention includes a method of treating a subject in need thereof, the method including parenterally administering to the subject a composition as described above and thereby treating the subject. In some embodiments, the composition is administered subcutaneously. In some embodiments, the composition is administered intravenously.

In some embodiments, administering the composition subcutaneously produces improved systemic pharmacokinetics relative to intravenously administration of the composition. In some embodiments, the improved pharmacokinetics comprises increased bioavailability. In some embodiments, the improved pharmacokinetics comprises increased Tmax for a subcutaneous injection compared to intravenous injection. In some embodiments, the improved pharmacokinetics comprises decreased Cmax for a subcutaneous injection compared to intravenous injection. In some embodiments, the improved pharmacokinetics comprises increased half-life of t½. In some embodiments, the improved pharmacokinetics comprises increased absorption rate.

In some embodiments, the subject has established type 1 diabetes (T1D) or type 2 diabetes (T2D). In some embodiments, the subject is in the honeymoon phase of T1D and has about 10-20% of their pancreatic beta cells relative to a healthy control, and produces insulin.

In some embodiments of the method, the method further includes administering a diabetes drug.

The present invention includes a device including a composition as described above, wherein the device is suitable for parenteral delivery of the composition. In some embodiments, the device is a syringe. In some embodiments, the device further includes a hypodermic needle assembly attached to the syringe. In some embodiments, the syringe further includes a protective cover around the needle assembly. In some embodiments, the needle is about ½ Inch to about ⅝ of an Inch in Length and has a Gauge of about 25 to about 31.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

DETAILED DESCRIPTION OF THE INVENTION

Figure 1:
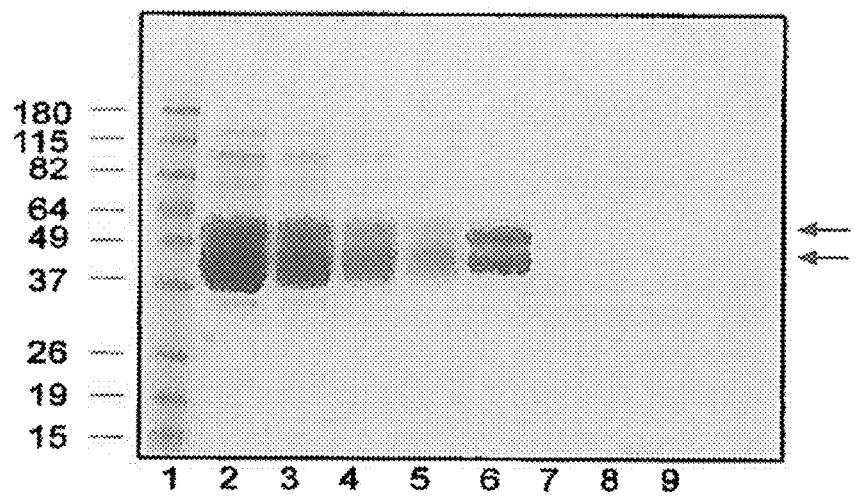
FIG. 1 is an SDS-PAGE gel stained with Coomassie Blue stain of various amounts of recombinant human KLK1 purified from CHO or 293 cell lines following transient transfection. Lane 1 is a pre-stained protein ladder, the molecular weights of the standards are written on the side (in kDa). Lanes 2-5 have KLK1 purified from CHO cells (lane 2, 14 µg protein; lane 3, 7 µg protein; lane 4, 3.5 µg protein; lane 5, 1.35 µg protein). Lane 6 has 14 µl of KLK1 protein purified from transient transfection of 293 cells. Lanes 7-9 are empty.

The present invention provides compositions of tissue kallikrein-1 (KLK1) that allow for improved absorption with parenteral administration. Such compositions are high concentration, liquid formulations of KLK1, at concentrations of up to about 100 mg/mL. Such high concentration formulations may advantageously be administered in a smaller volume injection. Also included are methods for the parenteral administration of such formulations to a subject in need thereof, where such administration has been surprisingly shown to improve the pharmacokinetic (PK) and pharmacodynamic (PD) parameters of KLK1 bioavailability.

Tissue kallikreins are members of a gene super family of serine proteases comprising at least 15 separate and distinct proteins (named tissue kallikrein 1 through 15) (Yousef et al., 2001, *Endocrine Rev;* 22:184-204). Tissue kallikrein-1 is produced predominantly in the pancreas, hence the origin of the name from the Greek term 'kallikrein.' It is also produced in the salivary glands and kidneys and is found in the urogenital tract and in skeletal muscle. Tissue kallikrein-1 is also known as KLK1, pancreatic/renal kallikrein, glandular kallikrein 1, kallikrein serine protease 1, kallikrein 1, renal kallikrein, renal/pancreas/salivary kallikrein, kidney/pancreas/salivary gland kallikrein. As used herein, the term "tissue kallikrein-1" and "KLK1" are synonymous.

Tissue kallikrein-1 is a trypsin-like serine protease. In humans and animal tissues, tissue kallikrein-1 cleaves kininogen into lysyl-bradykinin (also known as kallidin), a decapeptide kinin having physiologic effects similar to those of bradykinin. Bradykinin is a peptide that causes blood vessels to dilate and therefore causes blood pressure to lower. Kallidin is identical to bradykinin with an additional lysine residue added at the N-terminal end and signals through the bradykinin receptor.

The KLK1 gene encodes a single pre-pro-enzyme that is 262 amino acid residues in length and that includes the "pre-" sequence (residues 1-18) and the "pro-" sequence (residues 19-24), which is activated by trypsin-like enzymes. The mature and active form human KLK1 is a glycoprotein of 238 amino acid residues (residues 25-262) with a molecular weight of 26 kDa and a theoretical pI of 4.6. KLK1 has five disulphide bonds in its tertiary structure that are believed to be responsible for the protein's high stability, both against trypsin digestion and heat inactivation.

The amino acid sequence of tissue kallikrein-1 is available for a wide variety of species, including, but not limited to, human (SEQ ID NO:1 and SEQ ID NO:2), mouse (see, for example, GenBank: AAA39349.1, Feb. 1, 1994); domestic cat (see, for example, NCBI Reference Sequence: XP_003997527.1, Nov. 6, 2012); gorilla (see, for example, NCBI Reference Sequence: XP_004061305.1, Dec. 3, 2012); cattle (see, for example, GenBank: AAI51559.1, Aug. 2, 2007); dog (see, for example, CBI Reference Sequence: NP_001003262.1, Feb. 22, 2013); rat (see, for example, GenBank: CAE51906.1, Apr. 25, 2006); and olive baboon (see, for example, NCBI Reference Sequence: XP_003916022.1, Sep. 4, 2012). KLK1 is functionally conserved across species in its capacity to release the vasoactive peptide, Lys-bradykinin, from low molecular weight kininogen. A tissue kallikrein-1 polypeptide of the present invention may have any of the known amino acid sequences for KLK1, or a fragment or variant thereof.

In some aspects, a tissue kallikrein-1 polypeptide is a human tissue kallikrein-1 (hKLK1), including, but not limited to, a hKLK1 polypeptide represented by SEQ ID NO:1 or SEQ ID NO:2.

For example, hKLK1 may be represented by the amino acid sequence of GenBank Ref. NP_002248.1, having the complete KLK1 preprotein amino acid sequence shown below:

```
                                                              (SEQ ID NO: 1)
MWFLVLCLALSLGGTGAAPPIQSRIVGGWECEQHSQPWQAALYHFSTFQC                 50

GGILVHRQWVLTAAHCISDNYQLWLGRHNLFDDENTAQFVHVSESFPHPG                100

FNMSLLENHTRQADEDYSHDLMLLRLTEPADTITDAVKVVELPTEEPEVG                150

STCLASGWGSIEPENFSFPDDLQCVDLKILPNDECKKAHVQKVTDFMLCV                200

GHLEGGKDTCVGDSGGPLMCDGVLQGVTSWGYVPCGTPNKPSVAVRVLSY                250

VKWIEDTIAENS
```

Amino acids 1 to 18 of SEQ ID NO:1 represent the signal peptide, amino acids 19 to 24 represent propeptide sequences, and amino acids 25 to 262 represent the mature peptide. Thus, the preprotein includes a presumptive 17-amino acid signal peptide, a 7-amino acid proenzyme fragment and a 238-amino acid mature KLK1 protein.

As described in Example 1, a second amino acid sequence for human KLK1 is represented by SEQ ID NO:2, shown below:

```
                                                              (SEQ ID NO: 2)
MWFLVLCLALSLGGTGAAPPIQSRIVGGWECEQHSQPWQAALYHFSTFQC                 50

GGILVHRQWVLTAAHCISDNYQLWLGRHNLFDDENTAQFVHVSESFPHPG                100

FNMSLLENHTRQADEDYSHDLMLLRLTEPADTITDAVKVVELPTQEPEVG                150

STCLASGWGSIEPENFSFPDDLQCVDLKILPNDECKKVHVQKVTDFMLCV                200

GHLEGGKDTCVGDSGGPLMCDGVLQGVTSWGYVPCGTPNKPSVAVRVLSY                250

VKWIEDTIAENS
```

Again, amino acids 1 to 18 of SEQ ID NO:1 represent the signal peptide, amino acids 19 to 24 represent propeptide sequences, and amino acids 25 to 262 represent the mature peptide. Thus, the preprotein includes a presumptive 17-amino acid signal peptide, a 7-amino acid proenzyme fragment and a 238-amino acid mature KLK1 protein.

A comparison between SEQ ID NO:1 and SEQ ID NO:2 shows two amino acid differences between the two hKLK1 amino acid sequences. Single-nucleotide polymorphism (SNP's) between the two individuals within a species account for an E to Q substitution at amino acid residue 145 of 262 and an A to V substitution at position 188 of 262. SEQ ID NO:1 has an E (glutamic acid) at position 145 and an A (alanine) at position 188, while SEQ ID NO:2 has a Q (glutamine) at position 145 and a V (valine) at position 188.

A KLK1 polypeptide of the present invention may have an E at position 145; may have a Q at position 145; may have an A at position 188; may have an A at position 188; may have an E at position 145 and an A at position 188; may have a Q at position 145 and a V at position 188; may have an Q at position 145 and an A at position 188; or may have an E at position 145 and a V at position 188.

In certain embodiments, a tissue kallikrein-1 polypeptide may include residues 1-262, residues 19-262, or residues 25-262 of a kallikrein preproprotein sequence, including, but not limited to human KLK1 having SEQ ID NO:1 or SEQ ID NO:2, and fragments and variants thereof.

A "variant" of a starting or reference polypeptide is a polypeptide that has an amino acid sequence different from that of the starting or reference polypeptide. Such variants include, for example, deletions from, insertions into, and/or substitutions of residues within the amino acid sequence of the polypeptide of interest. A variant amino acid, in this context, refers to an amino acid different from the amino acid at the corresponding position in a starting or reference polypeptide sequence. Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A polypeptide variant may have at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity with a reference sequence, such as, for example, an amino acid sequence described herein.

In some aspects, a KLK1 polypeptide has at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity to SEQ ID NO:1, or to a fragment of SEQ ID NO:1, such as for example, residues 25-262 or residues 78-141 of SEQ ID NO:1. Such a KLK1 polypeptide may have an E or a Q at amino acid residue 145, and/or an A or a V at position 188.

In some aspects, a KLK1 polypeptide has at least about 80%, at least about 85%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% amino acid identity to SEQ ID NO:2, or to a fragment of SEQ ID NO:2, such as for example, residues 25-262 or residues 78-141 of SEQ ID NO:2. Such a KLK1 polypeptide may have an E or a Q at amino acid residue 145, and/or an A or a V at position 188.

"Percent (%) amino acid sequence identity" with respect to a polypeptide is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for measuring alignment, including any algorithms needed to achieve maximal alignment over the full length of the sequences being compared. The ALIGN-2 program is publicly available through Genentech, Inc., South San Francisco, Calif.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as follows:

100 times the fraction $X/Y$, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Variants may also include sequences added to the reference polypeptide to facilitate purification, to improve metabolic half-life or to make the polypeptide easier to identify, for example, an Fc region, a His-tag, and/or a PEGylation sequence.

The term "fragment" includes smaller portions of a KLK1 polypeptide that retain the activity of a KLK1 polypeptide. Fragments includes, for example, a KLK1 polypeptide fragment that ranges in size from about 20 to about 50, about 20 to about 100, about 20 to about 150, about 20 to about 200, or about 20 to about 250 amino acids in length. In other embodiments, a KLK1 polypeptide fragment ranges in size from about 50 to about 100, about 50 to about 150, about 50 to about 200, or about 50 to about 250 amino acids in length. In other embodiments, a KLK1 polypeptide fragment ranges in size from about 100 to about 150, about 100 to about 200, about 100 to about 250, about 150 to about 175, about 150 to about 200, or about 150 to about 250 amino acids in length. In other illustrative embodiments, a KLK1 polypeptide fragment ranges in size from about 200 to about 250 amino acids in length. Certain embodiments comprise a polypeptide fragment of a full-length KLK1 of about, up to about, or at least about 50, 60, 70, 80, 90, 100, 110, 120, 130, 140, 150, 160, 170, 180, 190, 200, 210, 220, 230, 240, 250 or more (e.g., contiguous) amino acid residues. In some embodiments, a fragment may have residues 25-262 or residues 78-141 of a preproprotein sequence. In some embodiments, a fragment may be any such fragment size, as described above, of SEQ D NO:1 or SEQ ID NO:2.

A fragments or variant of a KLK1 polypeptide may retain the enzymatic capacity to release the vasoactive peptide, Lys-bradykinin, from low molecular weight kininogen. In some embodiments, an active variant or fragment retains serine protease activity of a KLK1 polypeptide that releases kallidin from a higher molecular weight precursor such as kininogen, or that cleaves a substrate similar to kininogen such as D-val-leu-arg-7 amido-4-trifluoromethylcoumarin to release a colorimetric or fluorometric fragment.

A "wild type" or "reference" sequence or the sequence of a "wild type" or "reference" protein/polypeptide may be the reference sequence from which variant polypeptides are derived through the introduction of changes. In general, the "wild type" amino acid sequence for a given protein is the sequence that is most common in nature. Similarly, a "wild type" gene sequence is the polynucleotide sequence for that gene which is most commonly found in nature. Mutations may be introduced into a "wild type" gene (and thus the protein it encodes) either through natural processes or through human induced means.

In some embodiments of the formulations and methods of the present invention, human KLK (hKLK) may be used. One source of KLK1 has been isolation from pig pancreas. However, such porcine KLK1 preparations may have contamination with other porcine proteins, and have been formulated and administered orally in humans. Additionally, porcine KLK1 has 67% amino acid homology with human KLK1, and administration of procine KLK1 into human patients risks eliciting an immune reaction against porcine KLK1.

The KLK1 polypeptides described herein may be prepared by any suitable procedure known to those of skill in the art, including recombinant techniques. As one general example, KLK1 may be prepared by a procedure including one or more of the steps of: preparing a construct comprising a polynucleotide sequence that encodes a rhKLK1 and that is operably linked to a regulatory element; introducing the construct into a host cell; culturing the host cell to express the rhKLK1; and isolating the rhKLK1 from the host cell. The construct and expression system may be such that the mature or active rhKLK1 is expressed from the host cell. Alternatively, the rhKLK1 may be expressed in an inactive form, such as a propeptide, and the rhKLK1 serine protease activity may be activated (for example, by removing the "pro" sequence) after the rhKLK1 is isolated form the host cell.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (2001), and Ausubel et al., Current Protocols in Molecular Biology (2003).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell systems. If a non-mammalian cell expression system is used (such as bacteria) then a process would need to be used to add glycan groups to the rhKLK1, such as genetically engineered cells that express the enzymes required for mammalian style glycosylation.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan and Shenk, 1984, *PNAS USA;* 81:3655-3659). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., 1977, *J Gen Virol;* 36:59); baby hamster kidney cells (BHK, ATCC CCL 10); mouse sertoli cells (TM4, Mather, 1980, *Biol Reprod;* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., 1982, *Annals NY Acad Sci;* 383:44-68); MRC 5 cells; FS4 cells; and a human hepatoma line (Hep G2). Other useful mammalian host cell lines include Chinese hamster ovary (CHO) cells, including DHFR-CHO cells (Urlaub et al., 1980, *PNAS USA;* 77:4216)); and myeloma cell lines such as NSO and Sp2/0.

Exogenous DNA of the present invention obtained by genomic or cDNA cloning or by gene synthesis yields recombinant KLK1 (rKLK1) polypeptides. KLK1 polypeptide products of cell culture expression in vertebrate (e.g., mammalian and avian) cells may be further characterized by freedom from association with human proteins or other contaminants, which may be associated with KLK1 in its natural mammalian cellular environment or in extracellular fluids such as plasma or urine. Polypeptides of the invention may also include an initial methionine amino acid residue (at position-1). Certain embodiments therefore include host cells (e.g., eukaryotic host cells such as CHO cells, 293 cells) that comprise a recombinant or introduced polynucleotide that encodes a KLK1 polypeptide described herein, such as the polypeptide of SEQ ID NO:1 or SEQ ID NO:2. Also included are host cells that comprise a polynucleotide that encodes recombinant (e.g., non-naturally occurring) KLK-1 polypeptide described herein, such as the polypeptide of SEQ ID NO:1 or SEQ ID NO:2.

The cell culture expressed KLK1 polypeptides of the present invention may be isolated and purified by using, e.g., chromatographic separations or immunological separations involving monoclonal and/or polyclonal antibody preparations, or using inhibitors or substrates of serine proteases for affinity chromatography. As will be evident to those skilled in the art, the amino acid sequences of SEQ ID NO:1 and SEQ ID NO:2 list the sequence for pre-pro KLK1. If the gene coding for either of these sequences is expressed in mammalian cells, the 17-amino acid signal peptide (residues 1-18) should result in the KLK1 polypeptide to be secreted by the cell, and the signal peptide removed by the cell. If it is desired to not have the polypeptide secreted, or if non-mammalian cells are used for expression, a gene encoding KLK1 may be generated in which the signal sequence is omitted or replaced with another sequence. The 7 amino acid pro-sequence (residues 19-24) will inhibit the serine protease activity of the KLK1 and may be removed to allow activity of the mature KLK1 polypeptide. The pro-sequence may be removed after the KLK1 polypeptide is isolated, for example by exposing the pro-KLK1 to trypsin under conditions that will allow cleavage of the pro-sequence, or by generating a gene encoding KLK1 in which the pro-sequence omitted or replaced with another sequence.

In certain aspects, KLK1 polypeptides described herein may be "labeled" by covalent association with a detectable marker substance (such as, for example, radiolabels such as $I^{125}$ or $P^{32}$ and nonisotopic labels such as biotin) to provide reagents useful in detection and quantification of KLK1 in solid tissue and fluid samples such as blood or urine.

In addition to recombinant production methods, hKLK1 polypeptides may be produced by direct peptide synthesis using solid-phase techniques (see, for example, Merrifield, 1963, *J Am Chem Soc;* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired polypeptide. Also included is cell-free expression of proteins. These and related embodiments typically utilize purified RNA polymerase, ribosomes, tRNA and ribonucleotides; these reagents may be produced by extraction from cells or from a cell-based expression system.

The amino acid sequence of tissue kallikrein-1 indicates three potential Asn-linked (N-linked) glycosylation sites on the polypeptide, at amino acid positions 78, 84, and 141 (relative to the intact preproprotein amino acid sequence shown, for example, in SEQ ID NO:1), as well as putative O-linked glycosylation sites. For synthesis processes that do not result in glycosylated KLK1 polypeptides, a process may also be employed to add mammalian style, N-linked glycan groups at positions 78 and 84 to generate a double glycosylated glycoform of the KLK1 polypeptide or at positions 78, 84 and 141 to generate a triple glycosylated glycoform of the rhKLK1 polypeptide.

One source of human tissue kallikrein-1 is human urine, also known as human urinary KLK1 or HU KLK1. Several companies have isolated HU KLK1, formulated it into a pharmaceutical for administration to human patients for treatment of conditions such as cerebral infarction. However, technical challenges have not allowed HU KLK1 to be concentrated. As such, because of the dilute concentrations, large volumes of HU KLK1 have to be administered to human patients, requiring administration via intravenous (IV) administration.

Formulations of the present invention may provide advantages over naturally occurring sources of KLK1, such as urinary KLK1 (e.g., human KLK1 isolated from human urine). A KLK1 polypeptide as described herein may have higher levels of sialic acid compared to urinary KLK1. Such higher levels of sialic acid are expected to impart a more negative charge on the KLK1 protein, and result in a protein with a relatively low isoelectric point (pI). Such a low pI will result in the rhKLK1 protein having a net negative charge at physiological pH (~pH 7.4). In contrast, human urinary KLK1 will have a higher pI due to the presence of fewer sialic acids, and thus will not be as negatively charged at physiological pH. Protein formulations are ideally near physiological pH as a low or high pH can cause discomfort at the parenteral injection site, and/or tissue damage. The low pI of rhKLK1 will also improve solubility of the protein in a formulation near physiological pH. The low pI allows KLK1 to be concentrated without aggregating as the negative charges at physiological pH would repel and prevent aggregation of rhKLK1. Further, certain compositions comprise a high percentage of monomers of rhKLK1, with >95% appearing as a monomer or single peak by SEC HPLC (size exclusion-HPLC).

The glycosylation degree of rhKLK1 described herein mainly relies on the level of sialic acid in the carbohydrate chain. As determined by SDS-PAGE electrophoresis, the molecular weight of HU KLK1 is about 39-43 kDa. In comparison, the molecular weight of the rhKLK1 described herein is about 40-49 kDa. The rhKLK1 has a higher and broader electrophoresis band than HU KLK1, indicating its different degree of glycosylation, especially the different degree of sialylation. Therefore, rhKLK1 has more complex glycosylation composition than the native protein. The amount of sialic acid will influence the isoelectric point (pI) of the rhKLK1; specifically, increased sialic acid will result in decreased pI. In specific embodiments, the rhKLK1 described herein has a pI of less than about 5 and sialic acid content of at least 4 moles per mole protein. In some aspects, the sialic acid content (mole per mole rhKLK1 protein) may be about 4.05, 4.10, 4.15, 4.20, 4.25, 4.30, 4.35 or greater.

Certain embodiments include KLK1 that has increased sialic acid content of at least about 4 moles per mole protein and a resulting isolectric point of less than about 5 (pI<5), which can be formulated at concentrations greater than about 5 mg/mL, and which is substantially free of exogenous contaminants such as endotoxin. Such a concentrated rhKLK1 may be administered parenterally and has been shown to produce unexpectedly efficacious results.

Various methods are available to increase the sialic acid content of recombinant proteins. Such methods include the addition of certain sugars to the cell culture media, selecting production cell lines that produce well sialated proteins, or genetically engineering production cell lines to express enzymes necessary for silation, for example, CMP-sialic acid transporter (for review, see Bork et al., *J Pharm Sci* (2009) 98:3499-3508).

Several methods are available to determine sialic acid content including isoelectric focusing as described herein. Alternate methods for quantifying percent sialylation of glycoproteins include, High-Performance Anion Exchange Chromatography with Pulsed Amperometric Detection (HPAEC-PAD) combined with Matrix Assisted Laser Desorption/Ionization Time-of-Flight Mass Spectrometry (MALDI-TOF MS) have been used. For quantitative methods, Thiobarbituric Acid Assay (TAA), fluorescence method using o-phenylenediamine-2HCl (OPD) or malononitrile, derivatization, and enzymatic kits (Sigma, QA Bio, and Glycoscreen™ (ProZyme, San Leandro, Calif.) are some of the methods that can be used for quantifying sialic acid content of recombinant proteins produced in cell culture.

Purity.

Determinations of the purity of a composition of the present invention may include, but are not limited to, determination so endotoxin, host cell protein, host cell DNA, and/or percentage single peak purity by SEC HPLC.

Determination of Host Cell Protein.

Purity may be characterized in relation to the levels of host cell proteins. The host cells used for recombinant expression may range from bacteria and yeast to cell lines derived from mammalian or insect species. The cells contain hundreds to thousands of host cell proteins (HCPs) and other biomolecules that could contaminate the final product. The HCP may be secreted along with the protein of interest, or released by accidental lysing of the cells, and may contaminate the protein of interest. Two types of immunological methods may be applied to HCP analysis: Western blotting (WB) and immunoassay (IA), which includes techniques such as ELISA and sandwich immunoassay or similar methods using radioactive, luminescent, or fluorescent reporting labels. Compositions of the present invention may include host cell protein of less than about 500, less than about 400, less than about 300, less than about 200, less than about 100 or less than about 50 ng/mg total protein.

Determination of Host Cell DNA.

Purity can be characterized in relation to the levels of host cell DNA. Detection of residual host cell DNA may be performed by Polymerase Chain Reaction (PCR) with a variety of primers for sequences in the host cell genome. Residual host cell DNA is generally reported as being below a certain threshold level, but may also be quantitated with a rPCR method. Compositions of the present invention may include host cell deoxyribonucleic acid (DNA) of less than about 100, less than about 90, less than about 80, less than about 70, less than about 60, less than about 50, less than about 40, less than about 30, less than about 20, or less than about 10 pg/mg total protein.

Endotoxin Testing.

Endotoxin is extremely potent, is heat stable, passes sterilizing membrane filters and is present everywhere bacteria are or have been present. An Endotoxin Unit (EU) is a unit of biological activity of the USP Reference Endotoxin Standard.

The bacterial endotoxins test (BET) is a test to detect or quantify endotoxins from Gram-negative bacteria using amoebocyte lysate (white blood cells) from the horseshoe crab (*Limulus polyphemus* or *Tachypleus tridentatus*). Limulus amebocyte lysate (LAL) reagent, FDA approved, is used for all USP endotoxin tests. There are three methods for this test: Method A, the gel-clot technique, which is based on gel formation; Method B, the turbidimetric technique, based on the development of turbidity after cleavage of an endogenous substrate; and Method C, the chromogenic technique, based on the development of color after cleavage of a synthetic peptide-chromogen complex.

Two types of endotoxin tests are described in the USP <85> BET. Photometric tests require a spectrophotometer, endotoxin-specific software and printout capability. The simplest photometric system is a handheld unit employing a single-use LAL cartridge that contains dried, pre-calibrated reagents; there is no need for liquid reagents or standards. The FDA-approved unit is marketed under the name of Endosafe®-PTS™. The device requires about 15 minutes to analyze small amounts of sample, a 25 μL aliquot from CSP diluted in a sterile tube, and to print out results. In contrast, gel-clot methods require a dry-heat block, calibrated pipettes and thermometer, vortex mixer, freeze-dried LAL reagents, LAL Reagent Water (LRW) for hydrating reagents and depyrogenated glassware. In this clot test, diluted sample and liquid reagents require about an hour for sample and positive-control preparation and an hour's incubation in a heat block; results are recorded manually. Thus, the simplicity and speed of the automated system make it ideally suited to the pharmacy setting.

Purity SEC HPLC.

The degree of aggregation of rhKLK1 (isolated glycoform or mixture of glycoforms) may be determined by Size-exclusion chromatography (SEC), which separates particles on the basis of size. It is a generally accepted method for determining the tertiary structure and quaternary structure of purified proteins. SEC is used primarily for the analysis of large molecules such as proteins or polymers. SEC works by trapping these smaller molecules in the pores of a particle. The larger molecules simply pass by the pores as they are too large to enter the pores. Larger molecules therefore flow through the column quicker than smaller molecules, that is, the smaller the molecule, the longer the retention time. In certain embodiments, the "purity" of a KLK1 polypeptide in a composition may be specifically defined. For instance, certain compositions may include a hKLK1 polypeptide that is at least about 80, at least about 85, at least about 90, at least about 91, at least about 92, at least about 93, at least about 94, at least about 95, at least about 96, at least about 97, at least about 98, at least about 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds. Certain compositions are also substantially free of aggregates (greater than about 95% appearing as a single peak by SEC HPLC). Certain embodiments are free of aggregates with greater than about 96%, about 97%, about 98%, or about 99%, appearing as a single peak by SEC HPLC.

In certain embodiments, a high concentration KLK1 composition for parenteral administration is substantially pure, as determined by one or more of the following determinations of purity: less than about 1 EU endotoxin/mg protein, less that about 100 ng host cell protein/mg protein, less than about 10 pg host cell DNA/mg protein, and/or greater than about 95% single peak purity by SEC HPLC.

A high concentration formulation of KLK1 of the present invention may be formulated at a concentration of about 1 to about 200 mg/ml, about 2 to about 150 mg/ml, about 2.5 to about 100 mg/ml, about 5 to about 75 mg/ml, or about 10 to about 50 mg/ml.

In certain instances, the KLK1 is formulated at a concentration of about 1 to about 200 mg/ml, about 5 to about 200 mg/ml, about 10 to about 200 mg/ml, about 20 to about 200 mg/ml, about 25 to about 200 mg/ml, about 50 to about 200 mg/ml, about 75 to about 200 mg/ml, about 100 to about 200 mg/ml, about 125 to about 200 mg/ml, or about 150 to about 200 mg/ml.

In certain instances, the KLK1 is formulated at a concentration of 1 to about 100 mg/ml, about 5 to about 100 mg/ml, about 10 to about 100 mg/ml, about 20 to about 100 mg/ml, about 25 to about 100 mg/ml, about 50 to about 100 mg/ml, or about 75 to about 100 mg/ml.

In some embodiments, the concentration of the KLK1 polypeptide in a formulation of the present invention is greater than about 5 mg/mL, greater than about 10 mg/mL, greater than about 15 mg/mL, greater than about 20 mg/mL, greater than about 25 mg/mL, greater than about 50 mg/mL; greater than about 75 mg/mL, greater than about 100 mg/mL, greater than about 125 mg/mL, greater than about 150 mg/mL, or greater than about 175 mg/mL.

In some embodiments, the concentration of the KLK1 polypeptide in a formulation of the present invention is at least about 5 mg/mL, at least about 10 mg/mL, at least about 15 mg/mL, at least about 20 mg/mL, at least about 25 mg/mL, at least about 50 mg/mL; at least about 75 mg/mL, at least about 100 mg/mL, at least about 125 mg/mL, at least about 150 mg/mL, or at least about 175 mg/mL.

In some embodiments, the concentration of the KLK1 polypeptide in a formulation of the present invention is about 5 mg/mL, about 10 mg/mL, about 15 mg/mL, about 20 mg/mL, about 25 mg/mL, about 50 mg/mL; about 75 mg/mL, about 100 mg/mL, about 125 mg/mL, about 150 mg/mL, about 175 mg/mL, or about 200 mg/mL.

In certain embodiments, the KLK1 polypeptide has a pI of less than about 5 and a sialic acid content of at least about 4 moles per mole protein. Also included are compositions formulated for subcutaneous administration, comprising a recombinant human tissue kallikrein-1 (rhKLK1) polypeptide and a pharmaceutically acceptable carrier, where the concentration of the rhKLK1 polypeptide in the composition is greater than about 10 mg/mL, and where the rhKLK1 polypeptide has a pI of less than about 5 and a sialic acid content of at least about 4 moles per mole protein.

Methods for protein concentration. Several methods are known for concentrating proteins used as pharmaceuticals and may be used for the instant invention. One method is ultrafiltration, which concentrates a protein solution using selective permeable membranes. The function of the membrane is to let the water and small molecules pass through while retaining the protein. The solution is forced against the membrane by mechanical pump or gas pressure or centrifugation.

Formulations of KLK1 may be concentrated by lyophilization or freeze-drying. This process removes all volatile components (e.g., water or other solvents) leaving the proteins behind. Lyophylization works by freezing the protein solution and then reducing the surrounding pressure to allow the volatile components (e.g., water or other solvents) in the solution to sublimate directly from the solid phase to the gas phase. The protein may be partially lyophilized until the desired concentration is reached, or may be completely lyophilized and then solubilized in a smaller volume. Other methods may also be used, such as capturing the KLK1 on a capture column, and eluting with a small volume.

Drugs are often administered by two general methods, enteral and parenteral administration. Enteral administration involves administration by the gastrointestinal tract. Methods of enteral administration include oral, sublingual (dissolving the drug under the tongue), and rectal. Parenteral administration is administration other than through the digestive tract (alimentary canal), but rather by some other route. Parenteral administration may be by injection or infusion. Common injection types are intravenous (into a vein), subcutaneous (under the skin), intramuscular (into muscle), intraperitoneal, intravitreal (intraocular), intracerebral, and intraspinal. Infusions typically are given by intravenous route. Parenteral dosage forms may be solutions, suspensions, or emulsions, but they must be sterile. The KLK1 compositions described herein may be formulated for parenteral administration by a variety of techniques, including, for example, subcutaneous, intravenous, oral, rectal, transmucosal, transdermal, intestinal, parenteral, intramuscular, intramedullary, intrathecal, direct intraventricular, intraperitoneal, intranasal, and intraocular administration, among others.

In certain embodiments, the parenteral administration of a KLK1 formulation of the present invention demonstrates improved systemic pharmacokinetics. In particular embodiments, the improved pharmacokinetics comprises increased bioavailability. In some embodiments, the improved pharmacokinetics comprises decreased Tmax. In certain embodiments, the improved pharmacokinetics comprises increased Cmax. In some embodiments, the improved pharmacokinetics comprises increased absorption rate. In certain embodiments, subcutaneously administering the composition produces improved systemic pharmacokinetics relative to intravenously administering the composition.

For parenteral administration a high concentration KLK1 composition may be formulated with pharmaceutically acceptable carriers or excipients, for instance, to optimize stability and achieve isotonicity. In certain aspects, the pH of the formulation may be near physiological pH or about pH 7.4, including about pH 6.5, about 7.0, about 7.1, about 7.2, about 7.3, about 7.4, about 7.5, about 7.6, about 7.7, about 7.8, about 7.9, about 8.0, about 8.5, or any range thereof. In some embodiments, a composition (e.g., pharmaceutical composition) comprises a KLK1 polypeptide in combination with a physiologically acceptable carrier. Such carriers include pharmaceutically acceptable carriers, excipients, or stabilizers which are nontoxic to the cell or mammal being exposed thereto at the dosages and concentrations employed. Methods of formulation are well known in the art and are disclosed, for example, in Remington: The Science and Practice of Pharmacy, Mack Publishing Company, Easton, Pa., Edition 21 (2005).

In certain aspects, a formulation of KLK1 may be formulated to deliver a dose of a KLK1 of at least about 25 mg, or in the range of about 2 to about 5000 mg. In some embodiments, the dose may be at least about 0.02 to about 5.0 mg/kg/day, at least about 0.02 to about 1 mg/kg/day. In some embodiments, the dose may be at least about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0 mg/kg/day.

The phrase "physiologically-acceptable" or "pharmaceutically-acceptable" refers to molecular entities and compositions that do not produce a significant allergic or similar untoward reaction when administered to a human. Typically, such compositions are prepared as injectables, either as liquid solutions or suspensions; solid forms suitable for solution in, or suspension in, liquid prior to injection can also be prepared. The preparations can also be emulsified.

As used herein, "carrier" includes any and all solvents, dispersion media, vehicles, coatings, diluents, isotonic and absorption delaying agents, buffers, carrier solutions, suspensions, colloids, and the like. Except insofar as any conventional media or agent is incompatible with the active ingredient, its use in the therapeutic compositions is contemplated. Supplementary active ingredients can also be incorporated into the compositions.

Subcutaneous injection. A subcutaneous injection (abbreviated as SC, SQ, sub-cu, sub-Q or subcut with SQ being the preferred abbreviation) can be administered as a bolus into the subcutis, the layer of skin directly below the dermis and epidermis, collectively referred to as the cutis. Exemplary places on the body where people can inject SC most easily include, without limitation, the outer area of the upper arm, just above and below the waist, excepting in certain aspects the area right around the navel (a 2-inch circle), the upper area of the buttock, just behind the hip bone, and the front of the thigh, midway to the outer side, about 4 inches below the top of the thigh to about 4 inches above the knee. These areas can vary with the size of the person. Also, changing the injection site can prevent lumps or small dents called lipodystrophies from forming in the skin.

Subcutaneous injections usually go into the fatty tissue below the skin and in certain instances can utilize a smaller, shorter needle. In specific instances, a needle that is about ½ inch to about ⅝ of an inch in length with a gauge of about 25 to about 31 is sufficient to subcutaneously administer the medication. As will be appreciated by someone skilled in the art, these are general recommendations and SC injections may be administered with needles of other sizes. In some embodiments SC administration is performed by pinching-up on the tissue to prevent injection into the muscle, and/or insertion of the needle at a ~45° angle to the skin.

Intravenous injection is the injection of hKLK1 into a vein. The advantage of intravenous injection is that the hKLK1 is introduced into the circulation faster than if injected via other routes of administration.

Intramuscular injection is injection into the substance of a muscle, usually the muscle of the upper arm, thigh, or buttock. Intramuscular injections are given when the substance is to be absorbed quickly. They should be given with extreme care, especially in the buttock, because the sciatic nerve may be injured or a large blood vessel may be entered if the injection is not made correctly into the upper, outer quadrant of the buttock. The deltoid muscle at the shoulder is also used, but less commonly than the gluteus muscle of the buttock; care must be taken to insert the needle in the center, 2 cm below the acromion. Injections into the anterolateral aspect of the thigh are considered the safest because there is less danger of damage to a major blood vessel or nerve. The needle should be long enough to insure that the medication is injected deep into the muscle tissue. As a general rule, not more than 5 ml is given in an intramuscular injection for an adult. The needle is inserted at a 90-degree angle to the skin.

Intraperitoneal injections are not commonly performed in human patients due to discomfort, and are administered to obtain systemic blood levels of the agent; faster than subcutaneous or intramuscular injection and used when veins not accessible. The needle is introduced into the upper flank and the syringe plunger withdrawn to ensure that intestine has not been penetrated. The injected solution should run freely.

Intravitreal (intraocular) injections are injections into the eye and a small volume of injection is essential for these types of injections to avoid hypertension in the eye. The site of injection is usually inferotemporal for ease of access. Some Retina Specialists will do the injection in the superotemporal quadrant, as they feel that should a complication such as a retinal detachment form, it can be easier treated with a pneumatic retinopexy.

Intracerebral injection is an injection into the cerebellum or brain. Such injections would require a small injection volume to avoid localized hypertension that may result in damage to neuronal tissue.

Intraspinal (intrathecal) injection is the injection of a substance through the theca of the spinal cord into the subarachnoid space.

Dosing. The dosing of rhKLK1 will depend on various factors, including the disease to be treated, other medications that the patient is taking, etc. Dosing of rhKLK1 may also depend on the specific activity of the rhKLK1 protein. Dosages of rhKLK1 are usually administered based on the number of units, which are converted into mg of protein. rhKLK1 is a serine protease which cleaves low-molecular-weight kininogen resulting in the release of kallidin (lys-bradykinin) This activity of KLK1 may be measured in an enzyme activity assay by measuring either the cleavage of low-molecular-weight kininogen, or the generation of lys-bradykinin. Assays include examples wherein a labelled substrate is reacted with KLK1, and the release of a labelled fragment may be detected. One example of such a fluorogenic substrate suitable for KLK1 measurement of activity is D-val-leu-arg-7 amido-4-trifluoromethylcoumarin (D-VLR-AFC, FW 597.6) (Sigma, Cat # V2888 or Ana Spec Inc Cat #24137.) When D-VLR-AFC is hydrolyzed, the free AFC produced in the reaction can be quantified by fluorometric detection (excitation 400 nm, emission 505 nm) or by spectrophotometric detection at 380 nm (extinction coefficient=12,600 at pH 7.2). Other methods and substrates may also be used to measure KLK1 proteolytic activity.

KLK1 activity, measured in Units or Units/ml, may be determined by comparing the relative activity of a KLK1 sample to the porcine kininogenase standard acquired from the National Institute for Biological Standards and Control (NIBSC Product No. 78/543). For this standard, the assigned potency is 22.5 international units (IU) per 20 µg ampoule of porcine pancreatic kininogenase. Typically, serial dilutions are made of the standard, and the activity in an unknown sample of KLK1 is compared to the standard. For experiments described herein, the rhKLK1 glycoforms or mixtures had specific activities of approximately 200 to 450 IU/mg, though specific activities of certain lots may be outside this range. However, the specific activity of rhKLK1 may vary from lot to lot, and thus would need to be checked to determine the dosage in mg/kg or total mg of rhKLK1 to administer to an animal or patient.

According to the FDA Guidance for Industry; Estimating the Maximum Safe Starting Dose in Initial Clinical Trial for Therapeutics in Adult Healthy Volunteers (July 2005), Appendix D: Converting animal doses to human equivalent doses. A human equivalent dose is $\frac{1}{7}$ the rat dose and a human equivalent dose is $\frac{1}{12}$ a mouse dose.

As one non-limiting example, in some aspects, the rhKLK1 polypeptide is subcutaneously administered in an individual dose of at least about 200 µg/kg (0.20 mg/kg), or in range of about 20 µg/kg to about 5000 µg/kg (0.02 to 5.0 mg/kg). As one illustrative example, if rhKLK1 is administered at a dose of about 200 µg/kg into a 90 kg patient, then a total of about 18.0 mg of rhKLK1 would be required. If the rhKLK1 is formulated at 5 mg/mL, then a total of about 3.6 mL would be injected, which is a large volume and could cause discomfort if injected subcutaneously. However, if the rhKLK1 is formulated at 25 mg/mL, the total injection volume is 0.72 mL, which is within the recommended injection volume for subcutaneous delivery of 1.0 to 1.5 mL.

In particular embodiments a therapeutically effective amount of KLK1 includes an amount that lowers fasting glucose in a subject with type 2 diabetes or that increases glucose tolerance, or other indicator. Generally, an effective amount of KLK1 administered parenterally per dose includes 5.0 U/kg/day to about 1250 U/kg/day of patient body weight, although, as noted above, this is subject to therapeutic discretion. As an example, a dose may be 5.0 U/kg/day to 250 U/kg/day, or 5.0 U/kg/day to 150 U/kg/day of patient body weight.

For example, the dose of KLK1 may be increased if a patient's blood glucose is elevated above a predetermine levels (eg. greater than 180 mg/dl or greater than 200 mg/dl) immediately after meal or during a meal tolerance test or an OGTT or the dose is decreased if postabsorptive or fasting blood glucose levels are too low (for example, below approximately 80 mg/dl or below approximately 60 mg/dl).

The KLK1 dosage amount can be increased, merely by way of example, by about 1.1×, 1.2×, 1.3×, 1.4×, 1.5×, 1.6×, 1.7×, 1.8×, 1.9×, 2×, 2.5×, 3×, 3.5×, 4×, 4.5×, 5×, 6×, 7×, 8×, 9×, 10×, 15×, 20× or more, relative to the previous dosage. The dosage frequency can be increased, merely by way of illustration, by about 1, 2, 3, 4, 5 or more dosages per day, and/or 1, 2, 3, 4, 5, 6, 7, 8, 9, 10 or more dosages per week, relative to the previous dosing schedule. The dose of KLK1 may also be decreased by the amounts indicated above, such as a 0.95×, 0.90, 0.85, 0.80, 0.75, 0.70, 0.65, 0.60, etc. As noted above, the dosage amount can be increased or decreased separately or in combination with the dosage frequency, and vice versa, optionally until a desired level or range of glucose levels or other treatment indicators are achieved.

Alternatively, to administer a dose of about 500 µg/kg to a 90 kg person equates to about 45 mg of KLK1. If the KLK1 is formulated at 25 mg/mL, the injection volume is about 1.8 mL, which is above the recommended volume for subcutaneous injection. If the rhKLK1 is formulated at 50 mg/mL, the injection volume is about 0.9 mL or within the tolerable limit for subcutaneous injection into a human.

The compositions of the present disclosure can be administered by any suitable means including, but not limited to, for example, oral, rectal, nasal, topical (including, for example, transdermal, aerosol, buccal and sublingual), vaginal, parenteral (including, for example, subcutaneous, intramuscular, intravenous, intradermal, intravesical, intraperitoneal, intravitreal, intraocular, or intracerebral, intraspinal). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

A composition of the present invention may include one or more additional therapeutic modalities. In some aspects, the administration of a composition of the present disclosure may allow for the effectiveness of a lower dosage of other therapeutic modalities when compared to the administration of the other therapeutic modalities alone, providing relief from the toxicity observed with the administration of higher doses of the other modalities. One or more additional therapeutic agents may be administered before, after, and/or coincident to the administration of agents of the present disclosure. Agents of the present disclosure and additional therapeutic agents may be administered separately or as part of a mixture of cocktail. As used herein, an additional therapeutic agent may include, for example, an agent whose use for the treatment of diabetes is known to the skilled artisan.

A KLK1 composition as described herein may also be administered in combination with other drugs. A KLK1 composition described herein may be used to treat a patient with diabetes such as type 1 diabetes or type 2 diabetes and the subject many be administered a KLK composition and a known diabetes drug, known in the art to be useful in the treatment or prevention of insulin resistance and diabetes. Examples of diabetes drugs, include, for example, an antioxidant (such as vitamin E, vitamin C, an isoflavone, zinc, selenium, ebselen, or a carotenoid); an insulin or insulin analogue (such as regular insulin, lente insulin, semilente insulin, ultralente insulin, detemir, glargine, degludec, NPH or Humalog); an α-adrenergic receptor antagonist (such as prazosin, doxazocin, phenoxybenzamine, terazosin, phentolamine, rauwolscine, yohimbine, tolazoline, tamsulosin, or terazosin); a β-adrenergic receptor antagonist (such as acebutolol, atenolol, betaxolol, bisoprolol, carteolol, esmolol, metoprolol, nadolol, penbutolol, pindolol, propanolol, timolol, dobutamine hydrochloride, alprenolol, bunolol, bupranolol, carazolol, epanolol, moloprolol, oxprenolol, pamatolol, talinolol, tiprenolol, tolamolol, or toliprolol); a non-selective adrenergic receptor antagonist (such as carvedilol or labetolol); a first generation sulphonylurea (such as tolazamide, tolubtuamide, chlorpropamide, acetohexamide); a second generation sulphonylurea (such as glyburide, glipizide, and glimepiride); a biguanide agent (such as is metformin); a benzoic acid derivative (such as replaglinide); a α-glucosidase inhibitor (such as acarbose and miglitol); a thiazolidinedione (such as rosiglitazone, pioglitazone, or troglitazone); a phosphodiesterase inhibitor (such as anagrelide, tadalfil, dipyridamole, dyphylline, vardenafil, cilostazol, milrinone, theophylline, or caffeine); a cholineresterase antagonist (such as donepezil, tacrine, edrophonium, demecarium, pyridostigmine, zanapezil, phospholine, metrifonate, neostigmine, or galathamine); a glutathione increasing compound (such as N-acetylcysteine, a cysteine ester, L-2-oxothiazolidine-4-carboxolate (OTC), gamma glutamylcysteine and its ethyl ester, glytathtione ethyl ester, glutathione isopropyl ester, lipoic acid, cysteine, methionine, or S-adenosylmethionine); or incretin or incretin mimetics (such as GLP-1, GLP-2, glucagon like peptide analogues, such as DAC:GLP-1(CJC-1131), Liraglutide, ZP10, BIM51077, LY315902, LY307161 (SR), and exenatide). In some embodiments, the hKLK1 compositions are administered to a subject with insulin or an incretin mimetic.

The present invention includes methods of treating a subject in need thereof, comprising administering to the subject an effective amount of a composition as described herein. In some embodiments, the subject has established type 1 diabetes (T1D) or type 2 diabetes (T2D). In some embodiments, the subject is in the honeymoon phase, with the recent onset or diagnosis of type 1 diabetes T1D. The honeymoon, or remission phase, refers to the period following initial diagnosis when the remaining insulin producing beta cells are functioning well. During this honeymoon, it is easier to control blood sugars, with fewer swings, less risk for hypoglycemia, and lower overall average blood-sugar levels. The honeymoon period in type I diabetic patients is characterized by the preserved B cell function. In some embodiments, the subject in the honeymoon phase or recent onset of T1D has about 10-20% of their pancreatic beta cells relative to a healthy control and produces insulin. In some instances, the subject does not have type 1 diabetes (T1D) but is at risk for developing T1D. In some embodiments, the subject has type 2 diabetes, insulin resistance, pre-diabetes, diabetes, impaired glucose tolerance, impaired glucose metabolism, hyperglycemia, hyperinsulinaemia, and syndrome X. In some embodiments, the subject has latent autoimmune diabetes of adults (LADA). Type 2 diabetes (T2D) as used herein is a disease characterized by above normal levels of blood glucose. T2D may be caused by insufficient production of insulin in the subject or the subject being resistant to the action of insulin (insulin resistant). Administration of the compositions described herein to a subject with T2D may aid in moderating blood glucose levels.

In some embodiments, a therapeutically effective amount of a KLK1 composition includes an amount that lowers fasting glucose, increases glucose tolerance, or other indicator in a subject with diabetes. In some embodiments, a therapeutically effective dose is the amount of KLK1 glycoform composition that treats or delay the onset of type I diabetes without adverse side effects on blood pressure and heart rate.

In some embodiments, the subject has an ischemic condition. Non-limiting examples include cardiac ischemia (myocardial ischemia), ischemic colitis, brain ischemia (ischemic stroke), limb ischemia, and cutaneous ischemia. Also included is traumatic brain injury (TBI). These and related medical conditions can be diagnosed according to routine techniques in the art.

Devices.

The present invention also includes devices that contain a composition described herein, including devices suitable for parenteral delivery, including, for example, subcutaneous or intravenous delivery. In some embodiments, the device is a syringe. In some embodiments, the syringe is attached to a hypodermic needle assembly, optionally comprising a protective cover around the needle assembly. In some embodiments, the needle may be about ½ inch to about ⅝ of an inch in length and has a gauge of about 25 to about 31. Certain embodiments thus include devices that attached or attachable to a needle assembly that is suitable for subcutaneous administration, comprising a KLK1 glycoform mixture-based composition described herein. For example, certain devices include a vial or syringe, optionally where the vial or syringe is attachable to or is attached to a hypodermic needle assembly. Also included are vials having a rubber cap, where a needle/syringe can be inserted into the vial via the rubber cap to withdraw the KLK1-based composition for subcutaneous administration.

In particular aspects, the device is a syringe that is attachable or attached to a hypodermic needle, and is packaged with one or more removable and/or permanent protective covers around the needle or needle assembly. For instance, a first removable protective cover (which is removed during administration) can protect a user or other person from the needle prior to administration, and a second protective cover can be put (i.e., snapped) into place for safe disposal of the device after administration.

In certain aspects, a device, optionally a disposable device, comprises an individual dose of a KLK1 of at least about 25 mg, or in the range of about 2 to about 500 mg. In some embodiments, the device comprises a dose of at least about 0.02 to about 5.0 mg/kg, at least about 0.02 to about 10 mg/kg. In some embodiments, the device comprises a dose of at least about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0 mg/kg.

In certain aspects, the KLK1 composition may be packaged to allow administration by the patient or to the patient in a home setting on a daily basis, several times a week, weekly basis, or less frequently. A KLK1 composition may be formulated in a multi-dose vial or a multi-dose/multiuse syringe, similar to formulations of insulin or human growth hormone. In a multi-dose vial, an amount sufficient for at least 2 administrations may be in a vial (for example, 50 mg, or in the range of about 5 to 1000 mg), and a needle and syringe are used to draw the required amount of KLK1 from the vial and inject into a patient. In a multi-dose or multiuse syringe contains an amount of KLK1 sufficient for at least 2 administrations (for example, 50 mg, or in the range of about 5 to 1000 mg), and the volume that may be injected may be determined by the patient. The multi-dose syringe may also have a replaceable cartridge that may be loaded into the syringe that contains additional amounts of KLK1 composition.

A composition of the present invention may be endotoxin free or substantially endotoxin free. As used herein, the term "endotoxin free" or "substantially endotoxin free" relates generally to compositions, solvents, devices, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing KLK1 polypeptides in and isolating them from eukaryotic cells such as mammalian cells to reduce, if not eliminate, the risk of endotoxins being present in a composition of the invention. Preferred are methods of producing KLK1 polypeptides in and isolating them from recombinant cells grown in chemically defined, serum free media.

Endotoxins can be detected using routine techniques known in the art. For example, the *Limulus* Ameobocyte Lysate assay, which utilizes blood from the horseshoe crab, is a very sensitive assay for detecting presence of endotoxin. In this test, very low levels of LPS can cause detectable coagulation of the *limulus* lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml, or EU/mg protein. Typically, 1 ng lipopolysaccharide (LPS) corresponds to about 1-10 EU.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount or level produced by a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount or level produced a control composition, sample or test subject. One embodiment, the KLK1 has a decreased Cmax when composition of the invention is injected into a subject via a subcutaneous injection compared to intravenous injection. In another embodiment of the invention, the KLK1 has an increased Tmax when composition of the invention is injected into a subject via a subcutaneous injection compared to intravenous injection. In another embodiment of the invention, the KLK1 has an increased half-life or t½ when composition of the invention is injected into a subject via a subcutaneous injection compared to intravenous injection. Such decreased Cmax and increased Tmax may be beneficial if KLK1 is injected daily, to allow a slow release of KLK1 into the circulation and avoidance of peak followed by trough levels of KLK1.

Other examples of comparisons and "statistically significant" amounts are described herein. A result is typically referred to as "statistically significant" if it is unlikely to have occurred by chance. The significance level of a test or result relates traditionally to the amount of evidence required to accept that an event is unlikely to have arisen by chance. In certain cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see Goodman, *Ann Intern Med.* 130:1005-13, 1999).

The term "solubility" refers to the property of a rhKLK1 polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 6.0, pH 7.0, pH 7.4, pH 8.0 or pH 9.0. In certain embodiments, solubility is measured in water or a physiological buffer such as PBS or NaCl (with or without NaP). In specific embodiments, solubility is measured at relatively lower pH (for example, pH 6.0) and relatively higher salt (for example, 500 mM NaCl and 10 mM NaP). In certain embodiments, solubility is measured in a biological fluid (solvent) such as blood or serum. In certain embodiments, the temperature can be about room temperature (for example, about 20, about 21, about 22, about 23, about 24, or about 25° C.) or about body temperature (37° C.). In certain embodiments, a KLK1 polypeptide has a solubility of at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, or at least about 60 mg/ml at room temperature or at 37° C.

"Substantially" or "essentially" means nearly totally or completely, for instance, 95%, 96%, 97%, 98%, 99% or greater of some given quantity.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

A "subject," as used herein, includes any animal that exhibits a symptom, or is at risk for exhibiting a symptom, which can be treated with a KLK1 polypeptide or composition of the present invention. Suitable subjects (patients) include laboratory animals (such as mouse, rat, rabbit, or guinea pig), farm animals, and domestic animals or pets (such as a cat or dog). Non-human primates and, preferably, human patients, are included.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances such as host cell proteins or nucleic acids.

The present invention is illustrated by the following examples. It is to be understood that the particular examples, materials, amounts, and procedures are to be interpreted broadly in accordance with the scope and spirit of the invention as set forth herein.

EXAMPLES

Example 1

A cDNA coding for pre-pro-human KLK1, the 262 amino acid residue sequence depicted in SEQ ID NO:2, was purchased from OriGene™ (Rockville, Md., USA). The KLK1 cDNA (Catalogue No. SC122623) is a human cDNA open reading frame clone, cloned into the multi-cloning site of OriGene's pCMV6-XL5 vector, between a cytomegalovirus (CMV) promoter to control transcription of cDNA coding for pre-pro-human KLK1 and a polyadenylation signal. This KLK1 clone was sequenced and, using translation software, translated to reveal SEQ ID NO:2. This sequence differed at 2 amino acid residues from the human KLK1 sequence in GenBank as Ref No. NP_002248.1 (SEQ ID NO:1). As depicted in SEQ ID NO:2, single nucleotide polymorphisms (SNP's) resulted in an E to Q change at amino acid residue 145 of 262, and an A to V change at amino acid position 188 of 262. All subsequent experiments were performed with KLK1 having the amino acid sequence in SEQ ID NO:2.

The human KLK1 cDNA in the pCMV6-XL5 was transfected into a CHO cell line using the FreeStyle™ MAX CHO Expression System (Invitrogen, Carlsbad, Calif. Catalog no. K9000-20). The kit allowed for transient transfection of vectors into Chinese Hamster Ovary (CHO) cells, growth of the transfected CHO cells in 10 liter culture, and protein expression in defined, serum-free medium. The CHO cells are grown in suspension and transient transfection of the KLK1 vector was performed with the liposome reagent supplied in the kit as per instructions.

Expression and purification of recombinant human KLK1 were performed essentially as described by Hsieng S. Lu, et al, (Purification and Characterization of Human Tissue Prokallikrein and Kallikrein Isoforms Expressed in Chinese Hamster Ovary Cells, *Protein Expression and Purification* (1996), 8, 227-237). Briefly, following transfection and allowing sufficient time for expression of recombinant human KLK1, culture supernatant from the 10 liter culture of CHO cells was harvested by centrifugation followed by 0.2 micron filtration. Clarified supernatant was then concentrated, reacted with trypsin to activate the recombinant human KLK1. Because the transient transfection was performed with the cDNA coding for pre-pro-human KLK1, the recombinant human KLK1 secreted from the CHO cells was in an inactive proprotein form. Therefore, activity assay of cell culture supernatant KLK1 involves an activation step with trypsin digestion. Activation is done with trypsin at 10 nM final concentration for 2 hours at room temperature, and the trypsin inactivated with Soybean Trypsin Inhibitor (SBTI) (Sigma).

Following activation of the recombinant human KLK1, ammonium sulphate was added to the supernatant, and it was loaded onto an OCTYL SEPHAROSE® column. The Octyl column elution pool of active KLK1 was further purified by Benzamidine affinity column. Pooled active fractions off the Benzamidine column were then buffer exchanged into DEAE equilibration buffer and polished by DEAE column. Active KLK1 fractions from DEAE were pooled and buffer exchanged into 1×PBS buffer. The final KLK1 bulk drug substance was aliquoted and stored at −20° C.

Example 2

Figure 2:
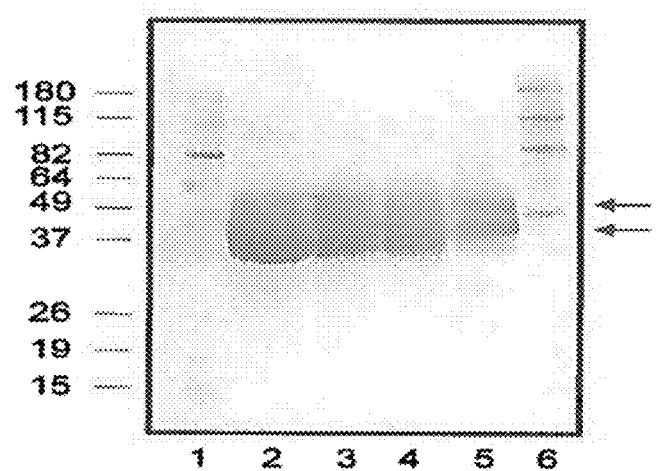
FIG. 2 is a Western blot stained with mouse anti-human KLK1 polyclonal antibodies of various amounts of recombinant human KLK1 purified from CHO or 293 cell lines following transient transfection. Lanes 1 and 6 are loaded with a pre-stained protein ladder, the molecular weights of the standards are written on the side (in kDa). Lanes 2-5 have KLK1 purified from CHO cells (lane 2, 5 µl protein; lane 3, 2.5 µl protein; lane 4, 1.25 µl protein). Lane 5 has 2.5 µl of KLK1 protein purified from transient transfection of 293 cells.

The purified recombinant human KLK1 contained approximately 30% carbohydrate content based on the molecular weight estimated by sodium dodecyl sulphate (SDS) polyacrylamide gel electrophoresis (see FIG. 1). KLK1 from CHO cells appears as a band having an apparent molecular weight of ~40 to 49 kDa; such a broad band may result from different glycosylation forms of KLK1 secreted by CHO cells. For KLK1 expressed in 293 cells, two bands appeared on the SDS-PAGE gel at approximately 40 kDa and 45 kDa. The identity of the bands as human KLK1 was confirmed by Western blot analysis using mouse polyclonal antibody raised against a full-length human KLK1 protein (Catalog # H00003816-B01P, KLK1 purified MaxPab mouse polyclonal antibody (B01P), Abnova Corporation, Walnut, Calif., USA) (see FIG. 2). The Western blot confirms the results of the SDS-PAGE gel, in that recombinant human KLK1 from CHO cells appears as a band having an apparent molecular weight of ~40 to 49 kDa, and KLK1 expressed in 293 cells resolves as two bands at approximately 40 kDa and 45 kDa.

The purity of rhKLK1 was relatively low endotoxin (<1 EU/mg protein) low host cell protein (<100 ng/mg protein), low host cell DNA (<10 pg/mg protein), and appeared substantially as a monomer (>95% single peak by SEC HPLC).

An enzyme activity assay was used to test for activity of recombinant human KLK1 in cell culture supernatants, chromatography fractions during purification and in the final purified product. One fluorogenic substrate suitable for tissue kallikrein-1 measurement of activity is D-val-leu-arg-7 amido-4-trifluoromethylcoumarin (D-VLR-AFC, FW 597.6) (Sigma, Cat # V2888 or Ana Spec Inc Cat #24137). When D-VLR-AFC is hydrolyzed, the free AFC produced in the reaction can be quantified by fluorometric detection (excitation 400 nm, emission 505 nm according to the catalogue, but alternate excitation and emissions are possible, including excitation 360 nm, emission 460 nm) or by spectrophotometric detection at 380 nm (extinction coefficient=12,600 at pH 7.2). The measurement of recombinant human KLK1 activity (Units/ml) produced in the CHO cells was determined by comparing the relative activity of recombinant KLK1 to the Kininogenase, Porcine standard acquired from the National Institute for Biological Standards and Control (NIBSC Product No. 78/543). For this standard, the assigned potency is 22.5 international units (IU) per 20 µg ampoule of porcine pancreatic kininogenase. All dosing of NOD mice was based on units of KLK1.

Figure 3A:
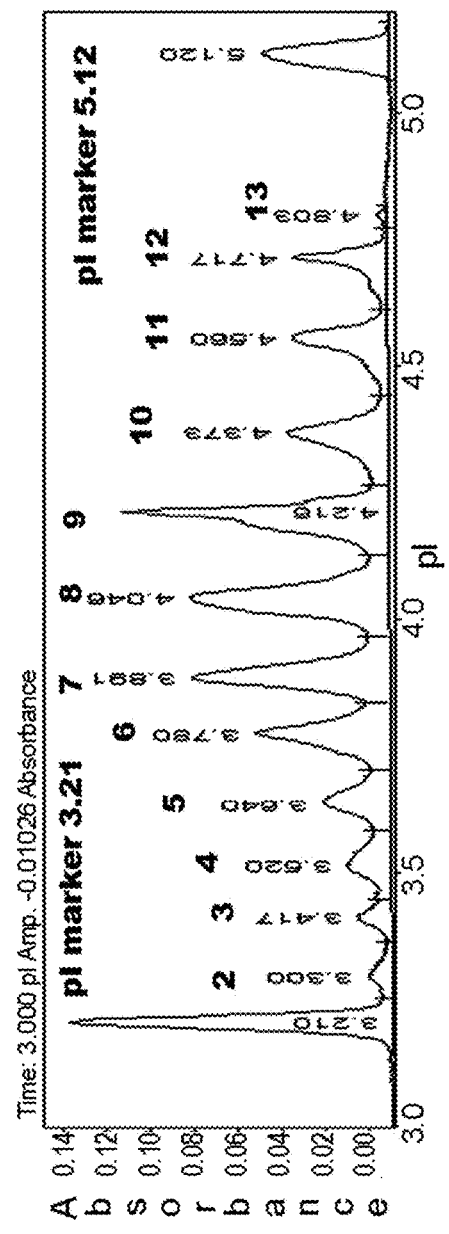
FIGS. 3A and 3B show capillary isoelectric focusing (cIEF) tracing of rhKLK1 samples determining the pI values among the various glycoforms, indicative of varying amounts of sialic acid. Markers are included with a pI of 3.21 and pI 5.12.
Figure 3B:
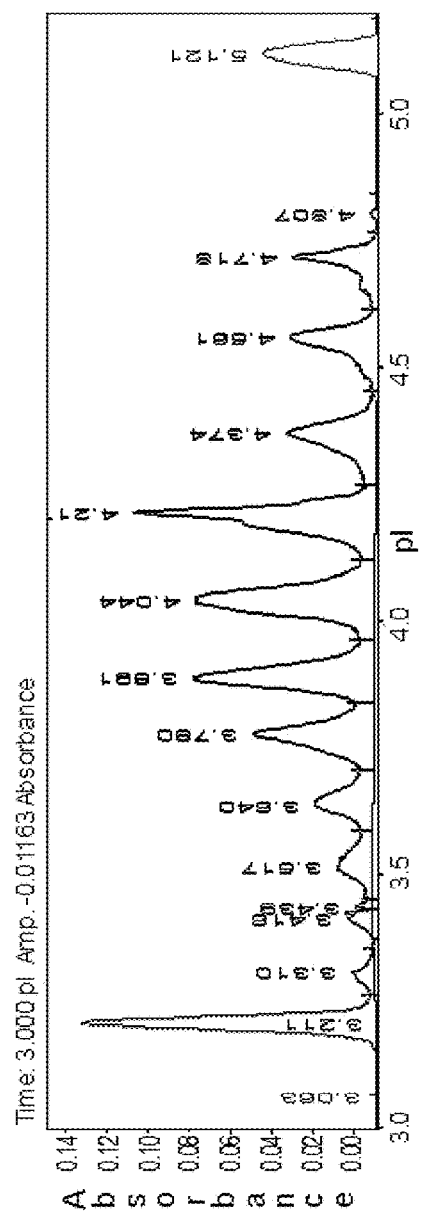

The rhKLK1 was analyzed by capillary isoelectric focusing (cIEF) to separate the various glycoforms with varying degrees of sialic acid by isoelectric point or pI. The rhKLK1 was separated by electrophoresis in a pH gradient between the cathode and anode. The rhKLK1 migrates through the gradient until its net charge is zero thus resulting in its isoelectric point (pI). Markers were used to indicate pI values of 5.12 and 3.21. The cIEF analysis method was conducted on an iCE280 cIEF analyzer equipped with a PrinCE microinjector. Two samples of rhKLK1 produced as described herein were analyzed, and the results are shown in FIG. 3 and summarized in Table 1 below. Twelve peaks were detected with pI's ranging from 4.81 to 3.30 (peak 1 is the marker pI 3.21).

TABLE 1

Capillary Isoelectric Focusing

| | Peak 1 | Peak 2 | Peak 3 | Peak 4 | Peak 5 | Peak 6 | Peak 7 | Peak 8 | Peak 9 | Peak 10 | Peak 11 | Peak 12 | Peak 13 |
|---|---|---|---|---|---|---|---|---|---|---|---|---|---|
| 1 | | 3.31 | 3.42 | 3.52 | 3.64 | 3.78 | 3.89 | 4.04 | 4.22 | 4.37 | 4.56 | 4.72 | 4.81 |
| 2 | | 3.30 | 3.42 | 3.52 | 3.64 | 3.78 | 3.89 | 4.05 | 4.22 | 4.37 | 4.56 | 4.72 | 4.80 |

To quantitate the sialic acid content, the rhKLK1 samples were analyzed by High Performance Anion Exchange Chromatography with Pulse Amperometric Detection (HPAEC-PAD). This method was accomplished by mild acid hydrolysis to release sialic acids from rhKLK1 followed by HPAEC-PAD to separate and quantify the recovered sialic acids. The HPAEC-PAD identifies the monosaccharides by comparing the retention time and electrochemical responses of monosaccharides released from rhKLK1 with those of standards of known concentrations. The result was 4.15 moles of sialic acid were detected per mole of protein.

Example 3

Generation of concentrated formulation of rhKLK1. The following example determined that rhKLK1 could be concentrated to at least 50 mg/mL, and that the resulting high concentration formulation would be stable and not aggregate.

The rhKLK1 having at least 4 moles sialic acid per mole protein was formulated into formulations having 5 mg/mL, 10 mg/mL, 25 mg/mL and 50 mg/mL. Bulk rhKLK1 was concentrated using VIVASPIN® 500 Centrifugal Concentrator 3,000 MWCO PES membrane. The protein concentration of rhKLK1 was determined by absorbance at 280 nm and the samples were close to the target concentration (5.0 mg/mL, 9.9 mg/mL, 26.2 mg/mL and 50.3 mg/mL). Following concentration, the samples were sterile filtered through a 0.2 µm filter. The rhKLK1 samples at the four different concentrations were filled into Schott borosilicate 3 cc, 13 mm serum vials at a fill volume of 0.5 mL, and the vials were sealed with a Daiko13 mm injection stopper, Flourotec Plus, B2-40 rubber stopper. The samples were stored at 2-8° C. and tested for aggregation via SEC HPLC on day 0 and day 7.

SEC HPLC was performed with a column TSKgel SW3000×L, 7.8 mm ID×30 cm, 5 µm particles (part #08541, column # T01819-175) and guard column: TSKgel guard SW×L, 60 mm ID×4.0 cm, 7 µm particles (part #08543, lot # T00281). The mobile phase was 10 mM sodium phosphate, 350 mM NaCl, pH 7.4, flow rate at 1.0 mL/min and detector set at 214 nm. Time=20 min and load=30 µg (30 µL at 1 mg/mL).

On day 0, all formulation appeared clear and free of visible particulates. On day 0, the SEC HPLC analysis of the four rhKLK1 formulations at different concentrations all revealed a single peak indicating there was no aggregation of rhKLK1 at any of the four concentrations tested. Analysis of the single peak and specifically calculation of the total area revealed the main single peak accounted for 100% of the rhKLK1 protein as monomers (see Table 2).

TABLE 2

| SEC HPLC T = Day 0 | | |
|---|---|---|
| Sample | % Main Peak | Total Area |
| Interim Ref. Std. (n = 3) | 100.0 | 40051.8 |
| rhKLK1 5 mg/mL | 100.0 | 40720.5 |
| rhKLK1 10 mg/mL | 100.0 | 39805.5 |
| rhKLK1 25 mg/mL | 100.0 | 42366.5 |
| rhKLK1 50 mg/mL | 100.0 | 41433.5 |

The four formulations were stored at 2-8° C. for 7 days. On day 7, the concentrations of rhKLK1 were determined in the samples. All formulations remain close to their target concentration and no significant differences were observed between formulations. All four formulations appeared clear and free of visible particulates on day 7. SEC HPLC analysis revealed a single peak (see FIGS. 4A and 4B). Analysis of the single peak and specifically calculation of the total area revealed the main single peak accounted for 100% of the rhKLK1 protein as monomers (see Table 3).

TABLE 3

| SEC HPLC T = Day 7 | | |
|---|---|---|
| Sample | % Main Peak | Total Area |
| Interim Ref. Std. (n = 3) | 100.0 | 40445.3 |
| rhKLK1 5 mg/mL | 100.0 | 40534.0 |
| rhKLK1 10 mg/mL | 100.0 | 40651.0 |
| rhKLK1 25 mg/mL | 100.0 | 42280.0 |
| rhKLK1 50 mg/mL | 100.0 | 42453.3 |

No significant differences were observed between formulations at day 7 as compared to time zero. No degradation of rhKLK1 observed after 7 days of storage at 2-8° C. Therefore, the rhKLK1 could be formulated at high concentrations (up to 50 mg/mL) and remain stable with no aggregation or other degradation.

Example 4

This example compared the pharmacokinetics and activity of recombinant human tissue kallikrein-1 (rhKLK1) when given by intravenous bolus and subcutaneous injection as a single dose to male Sprague Dawley rats.

TABLE 4

| Experimental Design | | | | | |
|---|---|---|---|---|---|
| Grp No. | No. of Animals[a] Male | Test Material/Route | Dose Level (mg/kg/dose) | Dose Concentration (mg/mL) | Dose Volume (mL/kg/dose) |
| 1 | 12 | rhKLK1/SC | 0.01049 (5 U/kg) | 0.00525 | 2 |
| 2 | 12 | rhKLK1/SC | 0.1049 (50 U/kg) | 0.0525 | 2 |
| 3 | 12 | rhKLK1/IV | 0.01049 (5 U/kg) | 0.00525 | 2 |
| 4 | 12 | rhKLK1/IV | 0.1049 (50 U/kg) | 0.0525 | 2 |

[a]Animals were euthanized on Day 3 after final study sample collections.

Animals. The Sprague-Dawley rat was chosen for this study as it is a species that has shown pharmacologic responses to rhKLK1, and is a species that is commonly used for nonclinical toxicity evaluations. The total number of animals used in this study (as well as the group size and number of groups) was considered to be the minimum required to properly characterize the pharmacokinetic properties of rhKLK1.

Male Sprague Dawley CRL:CD®IGS rats, approximately 8 weeks of age were purchase from Charles River Laboratories, Hollister, Calif. The rats were allowed to acclimate to the laboratory environment for a minimum of 7 days prior to the first day of dosing. Food (LABDIET® Certified CR 14% Protein Rodent Diet 5CR4) and water was provided ad libitum throughout the study. Each animal was identified by a cage label, tail marking, and/or radio frequency identification transponders. Animals were assigned to groups by a stratified randomization scheme designed to achieve similar group mean body weights. The animals were approximately 9 weeks of age at the time of initiation of dosing with body weights ranging from 252.2 to 310.1 grams.

The rhKLK1 was provided at a concentration of 1.28 mg/mL (610 U/mL or 476.56 U/mg), was diluted with PBS on Day 1 to yield dosing formulation at appropriate concentrations (0.00525 mg/mL and 0.0525 mg/mL). At this concentration, the rhKLK1 may be administered at 2 mL/kg/dose to achieve the final dose level.

Administration of rhKLK1 and vehicle control. The rhKLK1 was administered to animals in Groups 1 and 2 by subcutaneous injection once on Day 1. The dose volume for each animal was based on the most recent body weight measurement. The animal's back was clipped free of hair prior to the first dose. The animals were temporarily restrained for dose administration, and were not sedated. The volume for each dose was administered in one separate injection within the demarcated area.

The rhKLK1 was administered to animals in Groups 3 and 4 via intravenous (slow bolus) injection into a lateral tail vein once on Day 1. The dose volume for each animal was based on the most recent body weight measurement. The animals were temporarily restrained for dose administration, and were not sedated. Disposable sterile syringes were used for each animal/dose.

Clinical Observations. The following parameters and end points were evaluated in this study: clinical signs (mortality/moribundity checks and detailed clinical observations), body weights, body weight changes, food consumption, and bioanalytical and pharmacokinetic parameters. General health/mortality and moribundity checks were performed twice daily, in the morning and afternoon.

Results of clinical observations. Administration of rhKLK1 by single intravenous bolus or subcutaneous injection was well tolerated in male Sprague-Dawley rats at levels of 0.0149 or 0.1049 mg/kg. No rhKLK1-related effects were observed during the study period in mortality/moribundity, detailed clinical observations, body weights, body weight changes and food consumption.

Bioanalysis and Pharmacokinetic Evaluation Sample Collection. Blood was collected from the jugular (preferred) or lateral tail vein. Animals were not fasted for sample collections. Samples were collected at the following times after administration of rhKLK1: 5 min, 15 min, 30 min, 1 hr, 2, 4, 8, 12, 24, 48 and 72 hours. Blood samples were processed for plasma and were kept in a freezer set to maintain −80° C. Plasma samples were analyzed for concentration of test article. Several ELISA methods are known for detecting human KLK1 in serum or plasma and may be used. For example, a sandwich EILSA is described in WO/2004/029238 wherein rabbit anti-human KLK1 polyclonal immune globulin is coated onto a plate, and used to capture human KLK1. Here, the captured human KLK1 may be detected using labeled rabbit anti-human KLK1 polyclonal immune globulin. The capture and detection steps may also be performed with monoclonal antibodies, or a combination of polyclonal and monoclonal antibodies. For example, a monoclonal antibody that binds human KLK1 may be used to capture the human KLK1, and labeled polyclonal antibody to detect KLK1.

Pharmacokinetic Evaluation. Pharmacokinetic parameters were estimated using WInNONLIN® pharmacokinetic software (Pharsight Corp., Mountain View, Calif.). A noncompartmental approach consistent with the subcutaneous and IV routes of administration was used for parameter estimation. All parameters were generated from mean rhKLK1 concentrations in plasma from Day 1 unless otherwise stated. Mean concentrations were derived from 3 animals/group/time point/PK sampling occasion. Parameters were estimated using sampling times relative to the start of each dose administration.

The following pharmacokinetic parameters were estimated: $C_{max}$—the maximum observed arithmetic mean concentration of rhKLK1 measured after dosing; $C_{max}/D$—the $C_{max}$ divided by the dose administered; $T_{max}$—the time after dosing at which the maximum observed arithmetic mean concentration of rhKLK1 was observed; AUC(0-t)—the area under the rhKLK1 arithmetic mean concentration versus time curve from time zero the time after dosing at which the last quantifiable concentration of the drug was observed estimated by the linear or linear/log trapezoidal method; and AUC(0-t)/D—the AUC(0-t) divided by the dose administered.

When data permitted, the slope of the terminal elimination phase of each arithmetic mean concentration versus time curve was determined by log-linear regression, and the following additional parameters were also estimated.

In some instances, the following additional parameters were also measured: $T_{1/2}$—the apparent terminal elimination half life; AUC(0-inf)—the area under the arithmetic mean concentration versus time curve from time zero to infinity; AUC(0-inf)/D—the AUC(0-inf) divided by the dose administered; CL—the clearance, or the apparent volume of plasma cleared of rhKLK1 per unit time following intravenous dosing; and Vd—the apparent volume of distribution of rhKLK1, determined from the terminal elimination phase following intravenous dosing.

Bioanalysis and Pharmacokinetic Evaluations. Based on the ELISA total antigen testing, rhKLK1 was detected in plasma samples from the SC 0.1049 mg/kg/dose, IV 0.01049 mg/kg/dose, and IV 0.1049 mg/kg/dose groups. No measurable amount of rhKLK1 was detected in the 0.01049 mg/kg SC dosed group (rhKLK1 levels were below the level of detection for this ELISA).

For the subcutaneous 0.1049 mg/kg dose, the peak rhKLK1 mean plasma concentration (based on total antigen) was observed at 12 hours followed by a shallow monoexponential decline where the terminal elimination phase was not reached. For intravenous administration, the $T_{max}$ was observed at 15 min for the 0.01049 mg/kg dose and 5 min for 0.1049 mg/kg dose. Limited exposure did not allow for characterization of the terminal phase at 0.01049 mg/kg by intravenous administration. For the intravenous 0.1049 mg/kg dose, the peak KLK1 plasma concentration was followed by a monoexponential decline and $T_{1/2}$ was estimated to be about 6.44 hours. Volume of distribution (Vd) and clearance (CL) were 225 mL/kg and 24.2 mL/h/kg, respectively for the IV dose of 0.1049 mg/kg. Absolute bioavailability (SC/IV) was 583% for the 0.1049 mg/kg dose level. Because the rhKLK1 levels in rats injected SC did not decrease sufficiently from the peak levels within the 72 hrs, the $T_{1/2}$ for SC injection could not be accurately calculated. However, it appears the $T_{1/2}$ for rhKLK1 in rats following SC injection is greater than 24 hours.

The pharmacokinetic parameters of rhKLK1 in Male Sprague-Dawley rat plasma following subcutaneous injection of rhKLK1 (0.1049 mg/kg/dose) and intravenous bolus injection of rhKLK1 (0.01049 and 0.1049 mg/kg/dose) are summarized in Table 5 below.

TABLE 5

Pharmacokinetic Parameters of rhKLK1

| Dose Level (mg/kg/dose) | SubQ 0.1049 | IV 0.01049 | IV 0.1049 |
| --- | --- | --- | --- |
| $T_{max}$ (hrs) | 12 | 0.25 | 0.083 |
| $C_{max}$ +/− SE (ng/mL) | 507 +/− 143 | 57.4 +/− 35.4 | 960 +/− 182 |
| AUC (0-t) +/− SE (ng · h/mL) | 23185 +/− 1598 | 21.9 +/− 8.35 | 3979 +/− 361 |
| AUC (0-inf) | | NE | 4328 (ng · h/mL) |
| $T_{1/2}$ (hrs) | >24 | NE | 6.44 |
| $V_d$ | | NE | 225 (mL/kg) |
| CL | | NE | 24.2 (mL/h/kg) |
| $C_{max}$/Dose | 4830 | 5474 | 9148 |
| AUC (0-t)/Dose | 221016 | 2086 | 37936 |
| AUC (0-inf)/Dose | — | | 41260 |

Figure 4A:
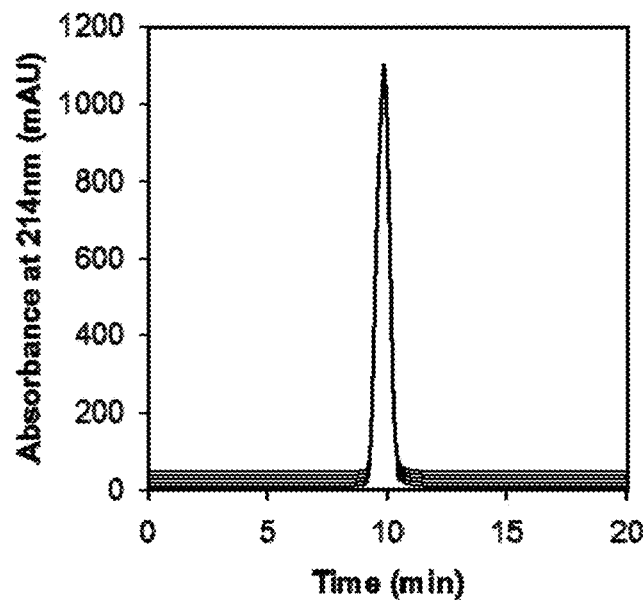
FIGS. 4A and 4B show a SEC HPLC analysis of rhKLK1 formulations at 5 mg/mL, 10 mg/mL, 25 mg/mL and 50 mg/mL after storage at 2-8° C. for 7 days.
Figure 4B:
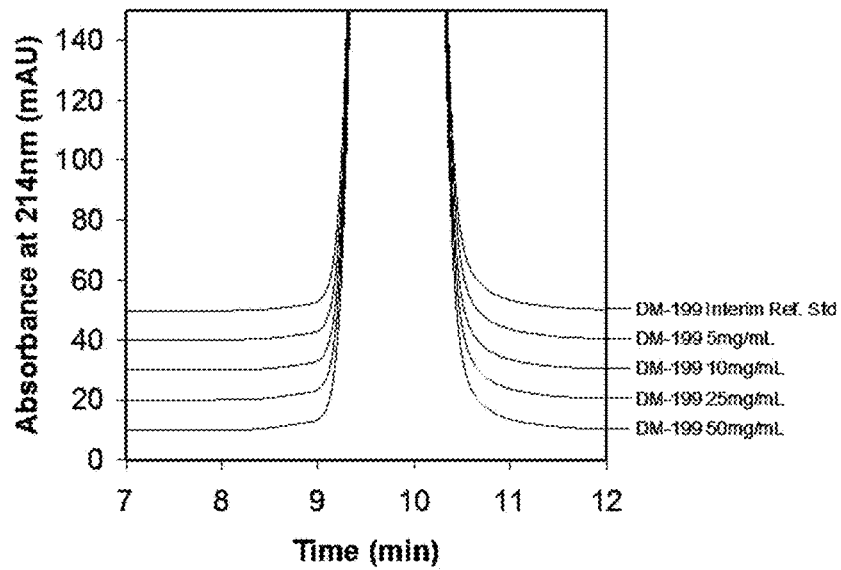
Figure 5A:
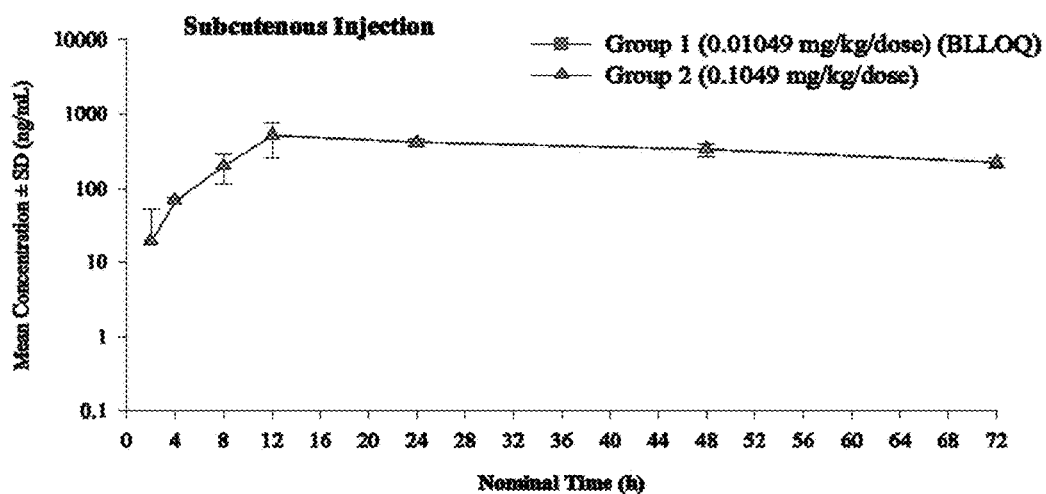
FIGS. 5A and 5B show the mean pharmacokinetic profiles of rhKLK1 in male Sprague-Dawley rat plasma following subcutaneous (5A) or intravenous (5B) bolus injection of rhKLK1.
Figure 5B:
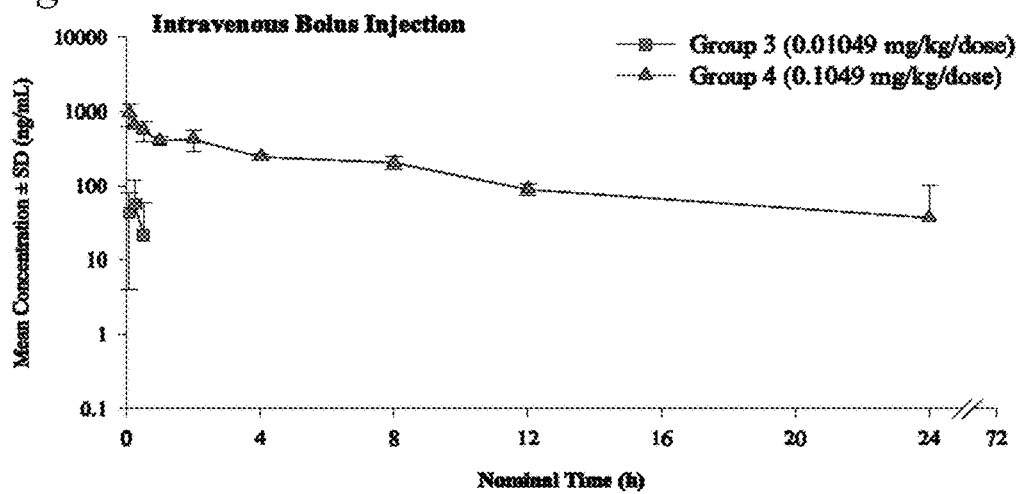

The absolute bioavailability of rhKLK1 in Male Sprague-Dawley rat plasma following subcutaneous or intravenous bolus injection of rhKLK1 is shown in FIG. 4A (subcutaneous) and FIG. 5B (intravenous) was calculated to be 53% based on Cmax and 583% based on AUC. The following formula was used to calculate Bioavailability for the 0.1049 mg/kg dose level of rhKLK1 based on AUC:

$$Fa(\%) = \{AUC(SC)/Dose(SC)\}/\{AUC(IV)/Dose(IV)\} \times 100$$
$$= 221016/37936 \times 100$$
$$Fa(\%) = 583$$

By definition, when a medication is administered intravenously, its bioavailability is 100%. However, when a medication is administered via other routes (such as subcutaneously), its bioavailability generally decreases. This is especially true for protein pharmaceuticals, where following subcutaneous administration some protein may be degraded while being absorbed into the circulation The data in FIGS. 5A and 5B surprisingly show improved bioavailability of rhKLK1 following subcutaneous administration relative to intravenous administration. For instance, at comparable dosages (0.1049 mg/kg/dose), these data show a slower yet relatively sustained increase in peak bioavailability of rhKLK1 during the first 12 hours post-subcutaneous administration, followed by a relatively slow decrease in rhKLK1 levels over then next 72 hours, compared to faster increase in peak bioavailability of rhKLK1 almost immediately post-intravenous administration, followed by a faster drop in rhKLK1 levels over the next 24 hours.

In a follow-on experiment, rhKLK1 was administered subcutaneously into Sprague Dawley rats at a very high dose (3.69 mg/kg) to measure the toxicokinetics. Male and female Sprague Dawley CRL:CD®IGS rats were received from Charles River Laboratories, Hollister, Calif. The animals were allowed to acclimatize for 5 days, and were provided LABDIET® Certified CR 14% Protein Rodent Diet 5CR4 and water ad libitum. A total of 6 male and 6 female rats were dosed with rhKLK1 at 3.69 mg/kg (1000 U/kg). The weight of the animals was between 377.6 to 421.1 g for the males and 217.2 to 248.0 g for the females.

The following parameters and end points were evaluated in this study: clinical signs (mortality/moribundity checks and detailed clinical observations), body weight changes, food consumption, clinical pathology parameters (hematology, coagulation, clinical chemistry, and urinalysis), toxicokinetic and anti-therapeutic antibody parameters, gross necropsy findings, organ weights, and histopathologic examinations.

There were no observed toxicity effects of rhKLK1 when given by subcutaneous (SC) injection once with a dose of 3.69 mg/kg and observed daily for 14 days. There were no rhKLK1 related organ weight changes, gross observations at necropsy, or microscopic findings on Day 15 in the animals in the tissues examined (subcutaneous injection site, brain, heart, kidney, liver, lung, pancreas, spleen and any gross lesions/masses).

Figure 6:
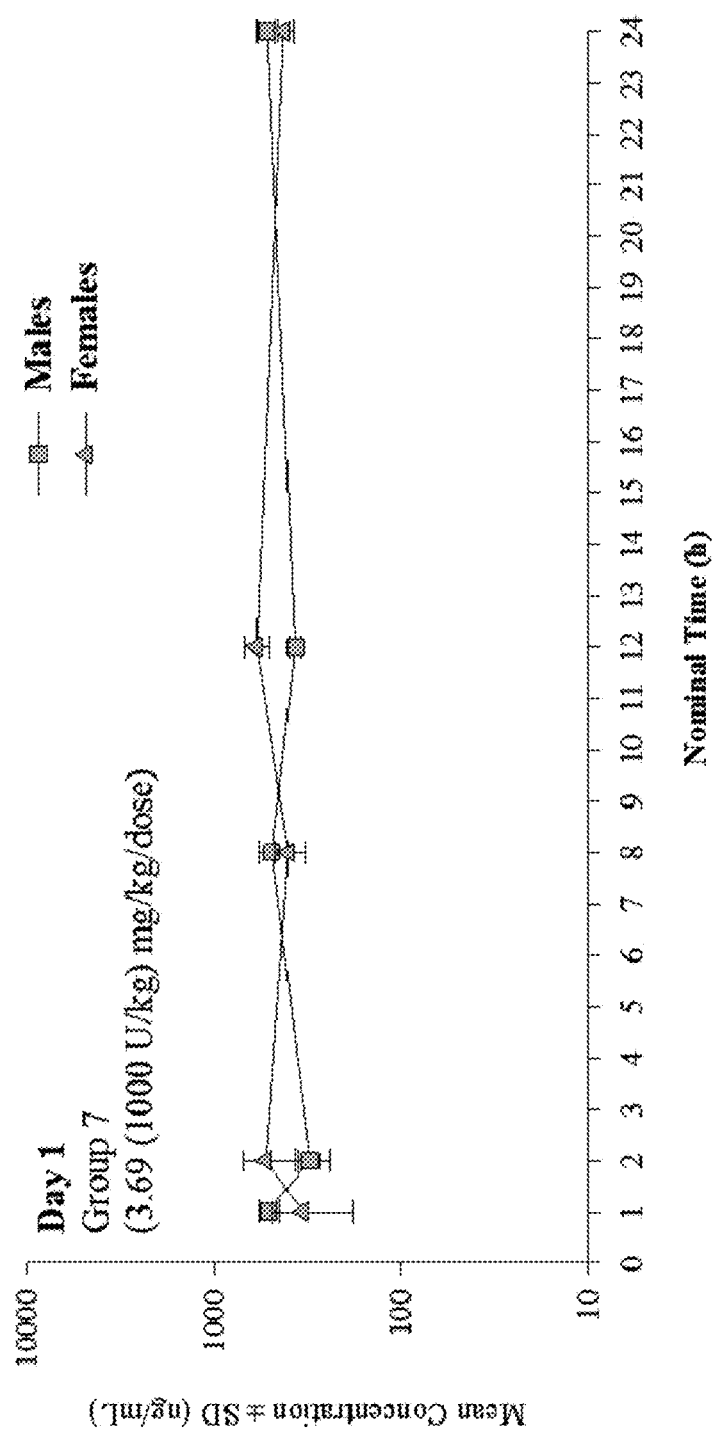
FIG. 6 shows the mean pharmacokinetic profiles of rhKLK1 in male and female Sprague-Dawley rat plasma following subcutaneous bolus injection of rhKLK1 at a dose of about 3.69 mg/kg.

Blood samples were drawn from the rats at 0 hr, 1 hr, 2 hr, 4 hr, 8 hr, 12 hr and 24 hr post injection. Blood samples were processed for plasma which was stored at −80° C. Plasma was analyzed for rhKLK1 levels by ELISA. The results are depicted graphically in FIG. 6 and specific parameters are tabulated in Table 6 below.

TABLE 6

Toxicokinetic parameters of rhKLK1 in rat plasma following subcutaneous injection

| | Tmax (h) | Cmax +/− SE (ng/mL) | AUC (0-t) +/− SE ng · h · mL | AUC (0-24) ng · h/mL | T½ |
|---|---|---|---|---|---|
| Males | 24 | 524 +/− 39.8 | 10163 +/− 526 | 10163 | NE |
| Females | 12 | 596 +/− 51 | 11543 +/− 624 | 11543 | NE |

No measurable amount of rhKLK1 was detected at time 0 as expected. All animals had detectable rhKLK1 concentrations in plasma post dose, and the levels were sustained until 24 hours postdose for the females and males. The terminal elimination phase and T ½ could not be characterized for males or females due to sustained peak concentrations. However, the T½ is greater than 24 hours. No gender differences in the Cmax and AUC values were observed.

Dosing rats at 3.69 mg/kg of rhKLK1 SC generated similar results to dosing at 0.1049 mg/kg, providing sustained rhKLK1 levels and improved systemic pharmacokinetics relative to intravenously administering the composition.

Example 5

Pharmacokinetics in Cynomolgus Monkeys

The pharmacokinetics of rhKLK1 in was characterized in male and female cynomolgus monkeys (2 males and 2 females) following subcutaneous injection at 1.80 mg/kg/day for 14 days. The Cmax of rhKLK1 was reached at 2 hours post-dose for the females and generally by 4 hours for the males. This gender difference in reaching Cmax is likely due to the small sample size and is unlikely to be detected in larger sample sizes.

Example 6

Toxicology Studies in Rats and Monkeys

A dose range-finding study was conducted in Sprague Dawley rats to determine the potential toxicity of rhKLK1 when given by single SC injection in a dose escalation study. Rats (N=3 males and 3 females per dose group) received single SC injections of 0.74 mg/kg, 1.85 mg/kg and 3.69 mg/kg. The following parameters and end points were evaluated in this study: clinical signs (mortality/moribundity checks and detailed clinical observations), body weight changes, food consumption, clinical pathology parameters (hematology, coagulation, clinical chemistry, and urinalysis), gross necropsy findings, organ weights, and histopathologic examinations. There were no observed toxicity effects of rhKLK1 when given by subcutaneous injection once during an escalating dose at a dose range of 0.74, 1.85 and 3.69 mg/kg.

An exploratory dose range-finding study was conducted in cynomolgus monkeys following single escalating subcutaneous injections of rhKLK1 to determine the potential toxicity of rhKLK1. Monkeys (one male and one female per dose group) were administered 0, 0.72 mg/kg and 1.80 mg/kg. The following parameters and end points were evaluated in this study: clinical signs, injection site observations, body weights, food consumption, clinical pathology parameters (hematology, coagulation, clinical chemistry, and urinalysis), blood pressure (via implantable telemetry), gross necropsy findings, organ weights, and histopathologic examinations. There were no observed toxicity effects of rhKLK1 when given by subcutaneous injection once during an escalating dose at a dose range of 0.72 and 1.80 mg/kg.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Sequence Listing Free Text

SEQ ID NO:1-2 Amino acid sequences of human tissue kallikrein-1 preproprotein

What is claimed is:

1. A method of treating a subject in need thereof, the method comprising subcutaneously administering to the subject a composition formulated for parenteral administration, the composition comprising a recombinant mature human tissue kallikrein-1 (hKLK1) polypeptide isolated from recombinant mammalian cells and a pharmaceutically acceptable carrier, where the mature hKLK1 polypeptide has a pI of less than about 5 and a sialic acid content of at least about 4 moles per mole protein, where the composition is substantially free of aggregates (greater than about 95% appearing as a single peak by SEC HPLC) and has endotoxin levels of less than about 1 EU/mg protein, host cell protein of less than about 100 ng/mg protein, and host cell DNA of less than about 10 pg/mg protein, and where administering the composition subcutaneously produces improved systemic pharmacokinetics relative to intravenous administration of the composition, thereby treating the subject.

2. The method of claim 1, where the improved pharmacokinetics comprises increased apparent half-life.

3. The method of claim 1, wherein the improved pharmacokinetics comprises decreased Tmax.

4. The method of claim 1, where the improved pharmacokinetics comprises increased absorption rate.

5. The method of claim 1, where the hKLK1 consists of an amino acid sequence with at least about 95% sequence identity to residues 25-262 of SEQ ID NO:1 or SEQ ID NO:2 and has serine protease activity.

6. The method of claim 5, where the serine protease activity is characterized by the ability to release kallidin from a higher molecular weight precursor.

7. The method of claim 5, where the hKLK1 polypeptide comprises residues 25-262 SEQ ID NO:1.

8. The method of claim 5, where the hKLK1 polypeptide consists of residues 25-262 SEQ ID NO:1.

9. The method of claim 5, where the hKLK1 polypeptide comprises residues 25-262 of SEQ ID NO:2.

10. The method of claim 5, where the hKLK1 polypeptide consists of residues 25-262 of SEQ ID NO:2.

\* \* \* \* \*

SEQUENCE LISTING

<160> NUMBER OF SEQ ID NOS: 2

<210> SEQ ID NO 1
<211> LENGTH: 262
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: PROPEP
<222> LOCATION: (19)..(24)
<220> FEATURE:
<221> NAME/KEY: mat_peptide
<222> LOCATION: (25)..(262)

<400> SEQUENCE: 1

Met Trp Phe Leu Val Leu Cys Leu Ala Leu Ser Leu Gly Gly Thr Gly
1               5                   10                  15

Ala Ala Pro Pro Ile Gln Ser Arg Ile Val Gly Gly Trp Glu Cys Glu
            20                  25                  30

Gln His Ser Gln Pro Trp Gln Ala Ala Leu Tyr His Phe Ser Thr Phe
        35                  40                  45

Gln Cys Gly Gly Ile Leu Val His Arg Gln Trp Val Leu Thr Ala Ala
    50                  55                  60

His Cys Ile Ser Asp Asn Tyr Gln Leu Trp Leu Gly Arg His Asn Leu
65                  70                  75                  80

Phe Asp Asp Glu Asn Thr Ala Gln Phe Val His Val Ser Glu Ser Phe
                85                  90                  95

Pro His Pro Gly Phe Asn Met Ser Leu Leu Glu Asn His Thr Arg Gln
            100                 105                 110

Ala Asp Glu Asp Tyr Ser His Asp Leu Met Leu Leu Arg Leu Thr Glu
        115                 120                 125

Pro Ala Asp Thr Ile Thr Asp Ala Val Lys Val Val Glu Leu Pro Thr
    130                 135                 140

Glu Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                165                 170                 175

Leu Lys Ile Leu Pro Asn Asp Glu Cys Lys Lys Ala His Val Gln Lys
            180                 185                 190

Val Thr Asp Phe Met Leu Cys Val Gly His Leu Glu Gly Gly Lys Asp
        195                 200                 205

Thr Cys Val Gly Asp Ser Gly Gly Pro Leu Met Cys Asp Gly Val Leu
    210                 215                 220

Gln Gly Val Thr Ser Trp Gly Tyr Val Pro Cys Gly Thr Pro Asn Lys
225                 230                 235                 240

Pro Ser Val Ala Val Arg Val Leu Ser Tyr Val Lys Trp Ile Glu Asp
                245                 250                 255

Thr Ile Ala Glu Asn Ser
            260

<210> SEQ ID NO 2
<211> LENGTH: 262
<212> TYPE: PRT
<213> ORGANISM: Homo sapiens
<220> FEATURE:
<221> NAME/KEY: SIGNAL
<222> LOCATION: (1)..(18)
<220> FEATURE:

```
<221> NAME/KEY: PROPEP
<222> LOCATION: (19)..(24)
<220> FEATURE:
<221> NAME/KEY: mat_peptide
<222> LOCATION: (25)..(262)

<400> SEQUENCE: 2

Met Trp Phe Leu Val Leu Cys Leu Ala Leu Ser Leu Gly Gly Thr Gly
1               5                   10                  15

Ala Ala Pro Pro Ile Gln Ser Arg Ile Val Gly Gly Trp Glu Cys Glu
            20                  25                  30

Gln His Ser Gln Pro Trp Gln Ala Ala Leu Tyr His Phe Ser Thr Phe
            35                  40                  45

Gln Cys Gly Gly Ile Leu Val His Arg Gln Trp Val Leu Thr Ala Ala
        50                  55                  60

His Cys Ile Ser Asp Asn Tyr Gln Leu Trp Leu Gly Arg His Asn Leu
65                  70                  75                  80

Phe Asp Asp Glu Asn Thr Ala Gln Phe Val His Val Ser Glu Ser Phe
                85                  90                  95

Pro His Pro Gly Phe Asn Met Ser Leu Leu Glu Asn His Thr Arg Gln
            100                 105                 110

Ala Asp Glu Asp Tyr Ser His Asp Leu Met Leu Leu Arg Leu Thr Glu
            115                 120                 125

Pro Ala Asp Thr Ile Thr Asp Ala Val Lys Val Val Glu Leu Pro Thr
            130                 135                 140

Gln Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                165                 170                 175

Leu Lys Ile Leu Pro Asn Asp Glu Cys Lys Lys Val His Val Gln Lys
            180                 185                 190

Val Thr Asp Phe Met Leu Cys Val Gly His Leu Glu Gly Gly Lys Asp
            195                 200                 205

Thr Cys Val Gly Asp Ser Gly Gly Pro Leu Met Cys Asp Gly Val Leu
    210                 215                 220

Gln Gly Val Thr Ser Trp Gly Tyr Val Pro Cys Gly Thr Pro Asn Lys
225                 230                 235                 240

Pro Ser Val Ala Val Arg Val Leu Ser Tyr Val Lys Trp Ile Glu Asp
                245                 250                 255

Thr Ile Ala Glu Asn Ser
                260
```